(12) United States Patent
Srinivasan et al.

(10) Patent No.: US 9,964,510 B2
(45) Date of Patent: May 8, 2018

(54) ELECTROLYTIC FOUR-CHANNEL DEVICE AND METHOD

(71) Applicant: DIONEX CORPORATION, Sunnyvale, CA (US)

(72) Inventors: Kannan Srinivasan, Tracy, CA (US); Sheetal Bhardwaj, Fremont, CA (US); Rong Lin, Santa Clara, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 1044 days.

(21) Appl. No.: 14/028,064

(22) Filed: Sep. 16, 2013

(65) Prior Publication Data
US 2015/0076005 A1    Mar. 19, 2015

(51) Int. Cl.
| G01N 27/00 | (2006.01) |
| G01N 27/333 | (2006.01) |
| B01J 47/12 | (2017.01) |
| B01D 61/46 | (2006.01) |
| G01N 30/96 | (2006.01) |
| B01D 61/50 | (2006.01) |

(52) U.S. Cl.
CPC ......... *G01N 27/333* (2013.01); *B01D 61/46* (2013.01); *B01D 61/50* (2013.01); *B01J 47/12* (2013.01); *G01N 30/96* (2013.01)

(58) Field of Classification Search
CPC ...... G01N 27/00; G01N 21/00; G01N 27/333; G01N 30/96; B01D 61/46; B01D 61/50; B01J 47/12
USPC .......................... 422/68.1, 81, 82.01; 205/789
See application file for complete search history.

(56) References Cited

U.S. PATENT DOCUMENTS

| 3,686,089 | A | | 8/1972 | Korngold et al. |
| 4,265,534 | A | * | 5/1981 | Remijan .......................... 356/2 |
| 4,455,233 | A | * | 6/1984 | Pohl et al. ................... 210/635 |
| 4,999,098 | A | | 3/1991 | Pohl et al. |
| 5,045,204 | A | | 9/1991 | Dasgupta et al. |
| 5,248,426 | A | * | 9/1993 | Stillian et al. ............... 210/635 |
| 5,316,630 | A | * | 5/1994 | Dasgupta ..................... 204/452 |
| 5,518,622 | A | * | 5/1996 | Stillian et al. ............... 210/635 |
| 5,569,365 | A | * | 10/1996 | Rabin et al. ................... 204/450 |
| 5,597,734 | A | * | 1/1997 | Small et al. .................. 436/161 |
| 5,633,171 | A | * | 5/1997 | Small et al. .................. 436/161 |
| 5,935,443 | A | * | 8/1999 | Anderson et al. ............ 210/656 |
| 6,027,643 | A | | 2/2000 | Small et al. |
| 6,077,434 | A | | 8/2000 | Srinivasan et al. |
| 6,508,985 | B2 | | 1/2003 | Small et al. |
| 6,562,628 | B1 | * | 5/2003 | Liu et al. ...................... 436/161 |

(Continued)

FOREIGN PATENT DOCUMENTS

| CN | 1744945 | 3/2006 |
| CN | 102735792 A | 10/2012 |

(Continued)

OTHER PUBLICATIONS

U.S. Appl. No. 13/674,738 to Srinivasan et al.
(Continued)

*Primary Examiner* — Brian J. Sines

(57) ABSTRACT

An electrolytic device includes four channels separated by three charged barriers. The device can be used to suppress an eluent stream containing separated sample analyte ions and/or to pretreat a sample stream containing unseparated analyte ions.

1 Claim, 19 Drawing Sheets

(56) References Cited

U.S. PATENT DOCUMENTS

| | | |
|---|---|---|
| 6,955,922 B1 | 10/2005 | Liu et al. |
| 7,329,346 B2 | 2/2008 | Liu et al. |
| 7,390,386 B2 | 6/2008 | Srinivasan et al. |
| 7,473,354 B2 | 1/2009 | Liu et al. |
| 7,892,848 B2 | 2/2011 | Riviello |
| 8,529,758 B2 | 9/2013 | Riviello |
| 8,597,571 B2 | 12/2013 | Riviello |
| 9,074,291 B2 | 7/2015 | Riviello |
| 2003/0127392 A1 | 7/2003 | Srinivasan et al. |
| 2003/0132163 A1 | 7/2003 | Srinivasan et al. |
| 2006/0057733 A1 | 3/2006 | Liu et al. |
| 2006/0186046 A1 | 8/2006 | Liu et al. |
| 2006/0231404 A1 | 10/2006 | Riviello |
| 2006/0254969 A1 | 11/2006 | Yamanaka et al. |
| 2008/0116139 A1 | 5/2008 | Liu et al. |
| 2009/0101582 A1 | 4/2009 | Liu et al. |
| 2012/0241378 A1 | 9/2012 | Riviello |

FOREIGN PATENT DOCUMENTS

| | | |
|---|---|---|
| EP | 0442224 A2 | 8/1992 |
| EP | 1867348 B1 | 12/2007 |
| JP | 05018948 | 1/1993 |
| JP | 2005515055 | 5/2005 |
| WO | 9402227 A1 | 2/1994 |
| WO | WO9418555 A1 | 8/1994 |
| WO | 9944054 A1 | 9/1999 |
| WO | 0204940 A1 | 1/2002 |
| WO | WO02071052 A2 | 2/2003 |
| WO | 2006113306 A2 | 10/2006 |
| WO | WO2006110860 A1 | 10/2006 |
| WO | 2013036353 A1 | 3/2013 |

OTHER PUBLICATIONS

Caliamanis et al., "Enhancement of conductormetric detection of weak acids in ion chromatography," J. of Chrom. A, 850, 85-98, 1999.

* cited by examiner

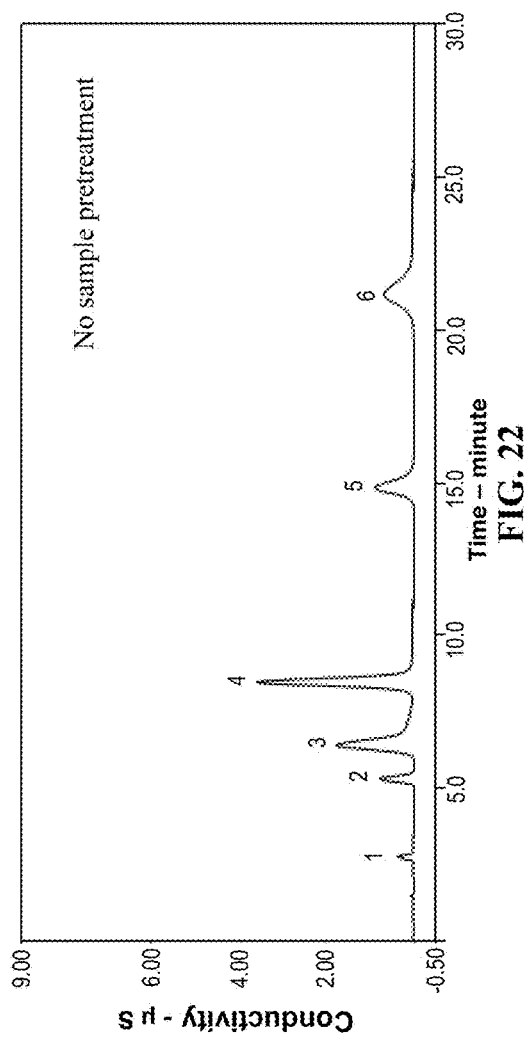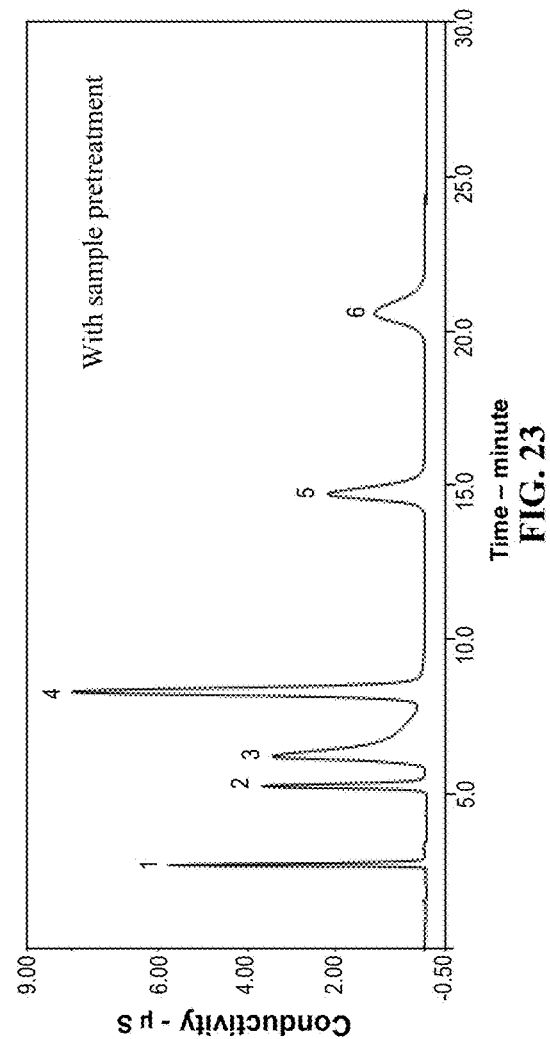

ELECTROLYTIC FOUR-CHANNEL DEVICE AND METHOD

BACKGROUND OF THE INVENTION

The present invention relates to an electrolytic device suitable for use in a liquid chromatographic system.

Suppressed ion chromatography is a known technique for analysis of sample ions of one charge in an eluent containing electrolyte. First, the sample ions in the eluent are chromatographically separated. Then, the eluent is suppressed by removal of the electrolyte counterions to the sample ions, and the sample ions are detected, typically by an electrical conductivity detector. One type of suppressor device, called a sandwich membrane suppressor, is described in U.S. Pat. No. 4,999,098 (the "'098 patent"). In one embodiment, the suppressor includes three channels. During suppression, the eluent and separated sample ions flow through the central channel of the suppressor while regenerant solution flows in the two outside channels. The outside two channels are separated from the central channel by barriers having exchangeable ions capable of passing ions of only one charge, positive or negative, and of blocking bulk liquid flow. Suitable barriers are ion-exchange membranes sold under the trademark Nafion®. One embodiment is an electrolytic, three-channel flat membrane suppressor illustrated in FIGS. 2 and 3 of the '098 patent. For an anion analysis, the eluent including the analyte anions which have been previously separated on a chromatographic column, comprising a packed bed of anion exchange resin, flows through the central channel. The ion-exchange membranes include exchangeable cations. Eluent cations are removed from the central channel and are drawn toward the negative electrode across the adjacent membrane barrier, as illustrated in FIG. 3 of the '098 patent. Thus, if sodium hydroxide is used as the electrolyte of the eluent, the sodium ion is removed from the central channel across the cation exchange membrane adjacent to the cathode. A three-channel device of this type has also been used for purposes other than suppression such as pretreatment of a liquid sample prior to chromatographic separation.

SUMMARY OF THE INVENTION

One embodiment of the invention is an electrolytic device suitable for use in a liquid chromatography system. The device comprises a housing including at least first, second, third, and fourth side-by-side liquid flow-through channels, each having an inlet and an outlet; said first channel being separated from said second channel by a first charged barrier having exchangeable ions capable of passing ions of only one charge, positive or negative, and of blocking bulk liquid flow; said second channel being separated from said third channel by a second charged barrier having exchangeable ions capable of passing ions of the same charge, positive or negative, and of blocking bulk liquid flow; said third channel being separated from said fourth channel by a third charged barrier having exchangeable ions capable of passing ions of the same charge, positive or negative, and of blocking bulk liquid flow; a first electrode disposed adjacent to and along said first channel in electrical communication therewith; and a second electrode disposed adjacent to and along said fourth channel in electrical communication therewith.

Another embodiment is a method for pretreating a liquid sample stream containing unseparated analytes of one charge, positive or negative, and counterions to said analyte ions and for suppressing eluent containing previously separated sample analytes of one charge, positive or negative, in the above electrolytic device. The method comprises flowing said eluent containing said separated analytes into said second channel inlet through said second channel and out said second channel outlet; flowing said liquid sample containing unseparated analytes into said third channel inlet through said third channel and out said third channel outlet; and applying an electric current between said first and second electrodes of opposite charge across said first, second, third and fourth channels to cause ions of opposite charge to said separated sample analytes in said liquid sample and eluent to flow toward the one of said two electrodes of the opposite charge to first charged barrier exchangeable ions to remove at least some of said counterions in said liquid sample stream exiting said third channel outlet and simultaneously suppressing said eluent flowing out of said second channel outlet.

Another embodiment is a method for suppressing eluent containing previously separated sample analytes of one charge, positive or negative, in the above electrolytic device to convert the separated analytes to acid or base form and for converting said acid or base form separated analytes in the suppressed eluent to salt form. The method comprises flowing said eluent containing said separated analytes into said second channel inlet through said second channel and out said second channel outlet; and flowing said eluent from said second channel outlet to said third channel inlet and through said third channel to said third channel outlet and thereafter to a second detector; said flow through said second and third channels being countercurrent.

A further embodiment is another method for treating a sample stream in the above electrolytic device. The method comprises flowing said sample stream into said second channel inlet through said second channel and out said second channel outlet; and flowing aqueous streams through said first, third and fourth channels.

BRIEF DESCRIPTION OF THE DRAWINGS

FIG. 22 is a chromatogram illustrating anion analysis using a concentration step and suppression without sample pretreatment.

FIG. 23 is a chromatogram illustrating anion analysis using a concentration step and suppression with sample pretreatment in accordance with FIG. 1.

DETAILED DESCRIPTION OF PREFERRED EMBODIMENTS

In general, the present invention relates to an electrolytic device including at least four channels and use of the device in analysis of a liquid samples containing analyte ionic species of one charge, positive or negative, e.g., for use in liquid chromatography, specifically suppressed ion chromatography.

The use of an electrolytic three-channel device for suppression in ion chromatography is illustrated in the '098 patent, the disclosure of which is incorporated by reference herein. A major difference of the present device from a three-channel device is the use of one or more additional channels. The device includes at least three charged barriers instead of the two barriers of the '098 patent, but otherwise may be of the same structure.

Figure 1:
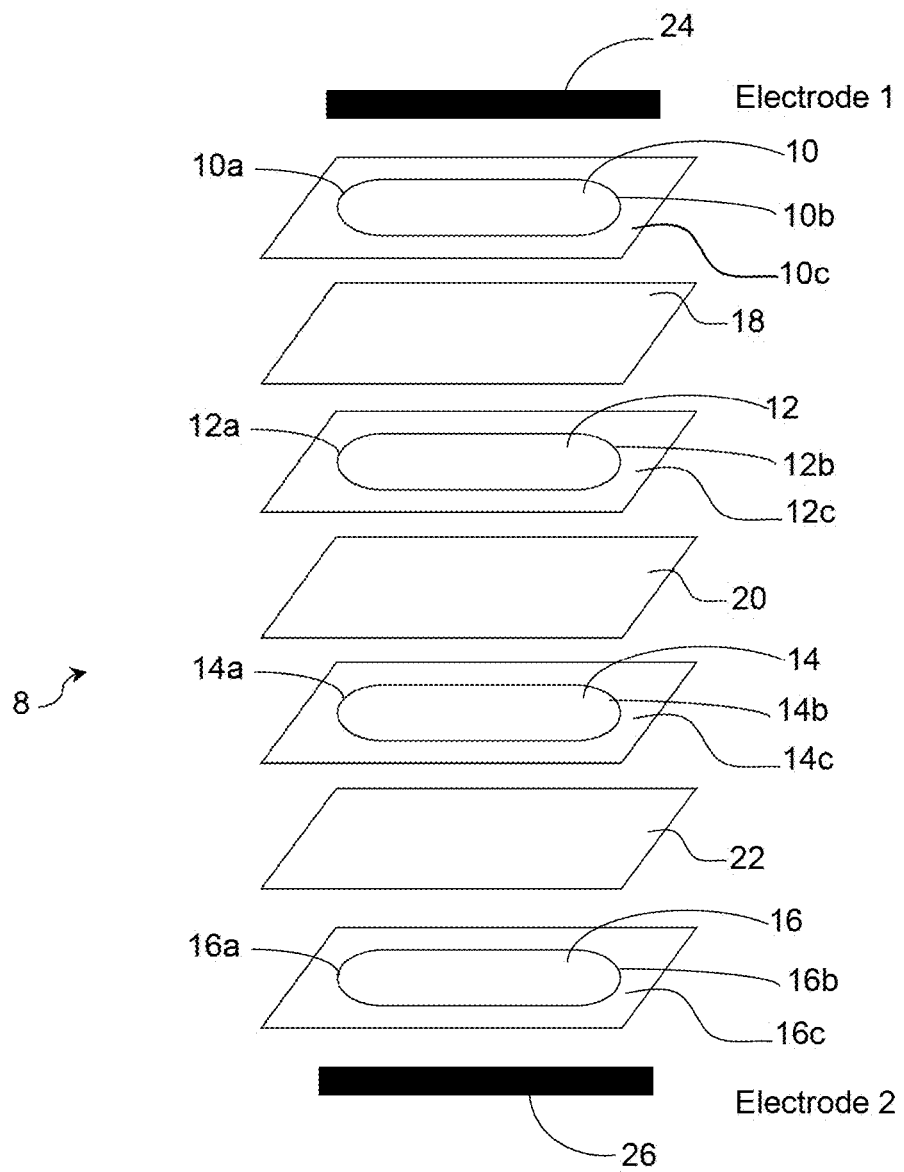
FIG. 1 is a schematic view of a four-channel electrolytic device according to the present invention.

FIG. 1 illustrates a schematic view of a four-channel device 8. The device includes a housing, not shown, such as of the type illustrated in FIG. 2 of the '098 patent but with suitable ports for the fluidic inlets and outlets. Device 8 defines first, second, third, and fourth side-by-side liquid flow channels, each having an inlet and an outlet. A first channel 10, including ports 10a and 10b, is defined by surrounding gasket 10c; a second channel, 12, including ports 12a and 12b, is defined by gasket 12c; a third channel, 14, including ports 14a and 14b is defined by gasket 14c; and a fourth channel, 16, including ports 16a and 16b, is defined by gasket 16c. The channels are side-by-side liquid flow-through channels. Channel 10 is separated from channel 12 by a charged barrier 18, having exchangeable ions capable of passing ions of only one charge, positive or negative, and of blocking bulk liquid flow. Channel 12 is separated from channel 14 by a charged barrier 20 of the same type as barrier 18. Channel 14 is separated from channel 16 by charged barrier 22, also of the same type as barrier 18.

It should be noted that the channels 10, 12, 14 and 16 can be defined by solid materials such as PEEK and have an elastomeric seal material adjacent to the barriers in place of the gasket material to make a seal on the perimeter of the channels 10, 12, 14 and 16. Hardware of this type is described in application entitled "Suppressor Device". (application Ser. No. 13/674,738, filed Nov. 12, 2012.)

A first electrode 24 is disposed adjacent to channel 10. A second electrode 26 is disposed adjacent to channel 16. Electrodes 24 and 26 may be in direct contact with the liquid flowing through channels 10 and 16, respectively, or may be separated from such liquids so long as the electrodes are in electrical communication with the liquid flowing through channels 10 and 16, respectively. For example, the electrodes 24 and 26 can be in direct contact with membrane 18 and 22. Electrodes 24 and 26 are connected to a conventional power source, not shown, so that, when the power is turned on, an electric field is applied between the electrodes across the liquid flowing through all four channels. At the anode, water is electrolyzed to hydronium ion and oxygen gas and at the cathode water is electrolyzed to hydroxide ion and hydrogen gas.

Flow-through structure such as neutral screens, or charged screens of the same charge as the exchangeable ions of the barriers not shown, may be disposed in one or more of the channels as illustrated in the '098 patent. Also, a bed of neutral particles or ion exchange particles may be disposed in the channels. In that regard, the structure of the electrolytic four-channel device, including the charged barrier separating the channels and the overall structure of the device, may be the same as that of the '098 patent, except for the additional barrier and the additional channel which may serve one of many functions such as set forth in the many applications for the device described hereinafter.

Figure 2:
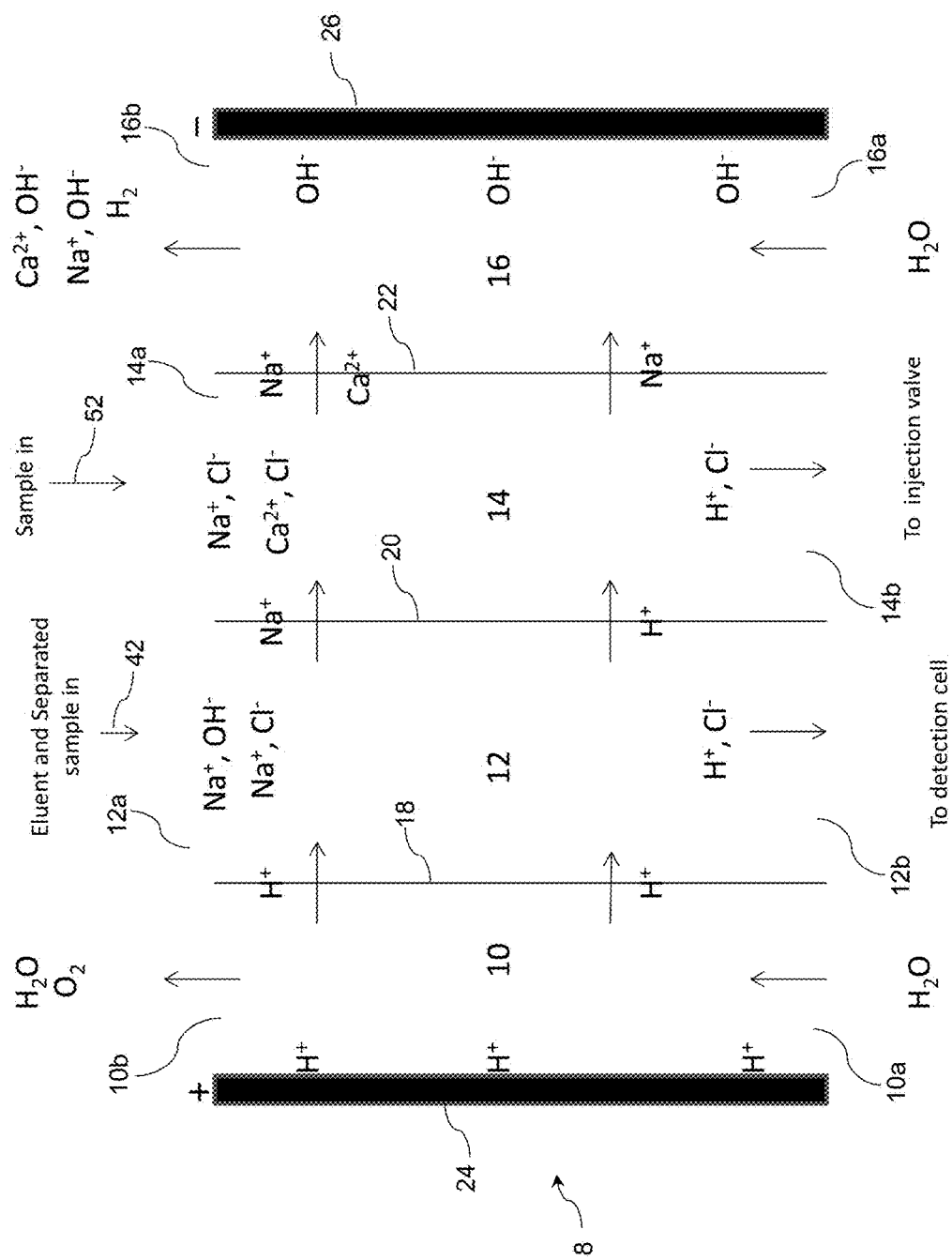
FIG. 2 is a schematic view of the device of FIG. 1 illustrating ionic flow when the device is used for a combination of sample pretreatment and suppression.
Figure 3:
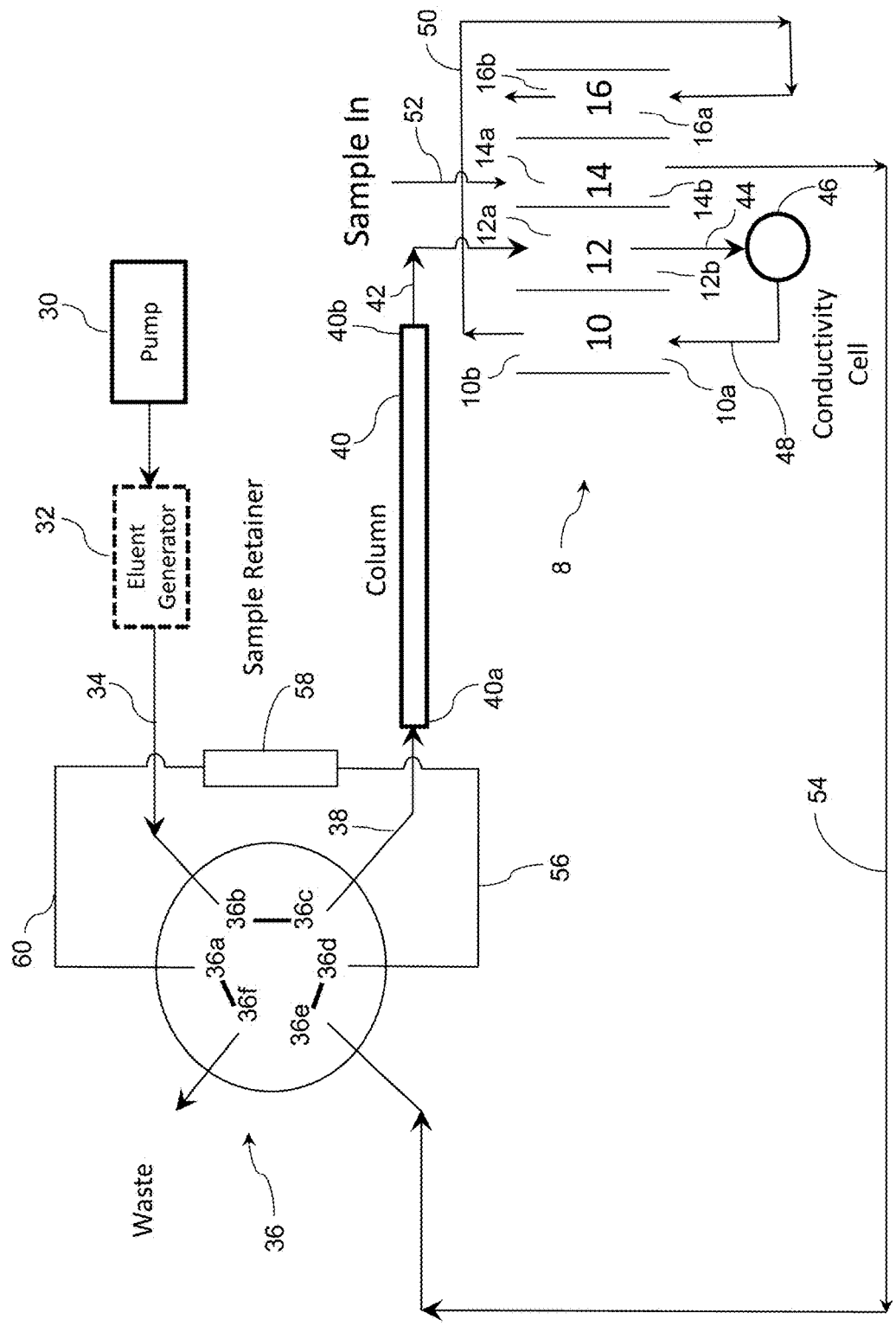
FIG. 3 is a schematic view of a system using the device of FIG. 2 with valving set in a position to pretreat the liquid sample in the device and to load the sample into a sample retainer.
Figure 4:
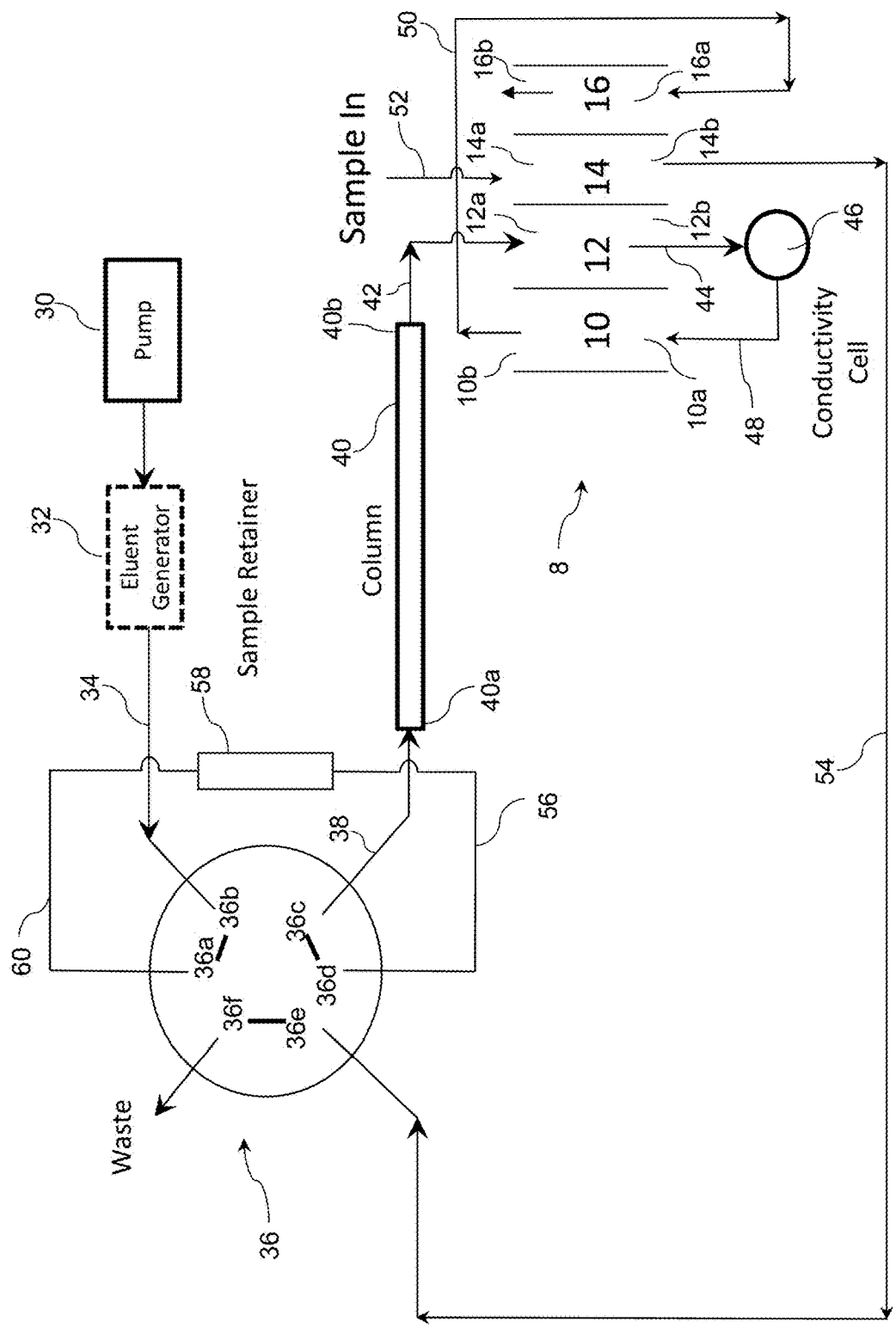
FIG. 4 is a schematic view of the apparatus of FIG. 3 with valving set for injection of the liquid sample in the sample retainer into a chromatography column.

FIGS. 2-4 illustrate a four-channel device used for a combination of sample pretreatment and suppression. Like parts will be used to designate like numbers for the four-channel device of FIG. 1.

Referring to FIG. 3, the sample pretreatment and suppression system is used with valving set in a first position for loading of the sample into a concentrator or sample loop, referred to collectively herein as "a sample retainer". As illustrated, a pump 30 pumps eluent from an optional eluent generator 32 through line 34 to valving 36 in the form of a six-way valve set for loading of the sample into the sample retainer 58. Alternatively, other types of single or multiple valves must also be used. Valving 36 includes six ports, 36 a-f. As illustrated, ports 36b and 36c are open so that eluent in line 34 flows in line 38 to a chromatographic separator 40 such as chromatography column, including an inlet 40a and an outlet 40b, of a conventional type, e.g., including a packed bed of ion exchange packing, and from there in line 42 to port 12a of channel 12 of the four-channel device 8. Separator outlet 40b is upstream of and in fluid communication with channel inlet 12a and outlet 12b is upstream of and in fluid communication with detector 46. In the sample loading setting of valving 36, the liquid stream flowing through channel 12 may include no sample. The liquid stream exiting outlet 12b flows in line 44 to a detector 46, illustrated as a conductivity cell, and from there in line 48 to inlet port 10a of channel 10 and out outlet port 10b to line 50 to recycle into inlet port 16a of channel 16 and out outlet port 16b to waste. This stream may be used as a source of water for other electrolytic devices and to carry waste streams carrying ions and gases.

Referring again to FIG. 3, in this first positioning of valving 36 for sample loading, a liquid sample stream flows to inlet port 14a of channel 14 and out outlet port 14b in line 54 to ports 36e and 36d to a sample retainer 58 in the form of a concentrator column or sample loop of a conventional type. If sample retainer 58 is a concentrator column, the sample ions of one charge, positive or negative, are retained in retainer 58, typically a packed ion-exchange resin bed with exchangeable ions of the same charge as the sample ions, and the remaining eluent flows in line 60 through ports 36a and 36f to waste. If sample retainer 58 is a sample loop, a measured amount of sample is retained in a sample loop. In this position of valving 36, sample is loaded in sample retainer 58 for a sample injection into the system as illustrated in FIG. 4 with valving 36 set in the second position.

A conventional eluent is provided, such as a cation hydroxide, e.g., sodium hydroxide or potassium hydroxide for anion analysis. The eluent generator 32 may be of a conventional type, such as illustrated in U.S. Pat. No. 6,955,922. Alternatively, eluent may be provided from a source, not shown, such as an eluent reservoir.

Referring to FIG. 4, in a second position of valving 36, set for sample injection into column 40, eluent from eluent generator 32 is pumped by pump 30 in line 34 through ports 36b and 36a through line 60 to carry sample in sample retainer 58 in line 56 through ports 36d and 36c to line 38 to inlet port 40a of chromatographic separator 40 and out outlet port 40b through line 42 into channel 12 and from there through detector 46, channel 10 and channel 16 to waste. Sample containing ions, positive or negative, are separated in column 40. Suppression takes place in channel 12, as will be described. The suppressed liquid sample flows in the eluent stream through detector 46, in which the separated sample analyte ions are detected. As is conventional, a suppressor suppresses the conductivity of the electrolyte ions of the eluent of effluent from column 40 which are of opposite charge to the ions being detected. Thus, for sample anion analysis, the suppressed eluent electrolyte ion is of opposite charge to the sample anions, i.e., a cation. Thus, for anion analysis, the electrolyte can be sodium hydroxide or potassium hydroxide or a salt such as sodium or potassium carbonate and/or bicarbonate.

When detector 46 is a conductivity cell, the presence of ionic species produces an electrical signal proportional to the amount of ionic material. Such signal is typically directed from the conductivity cell to a conductivity meter permitting detection of the concentration of separated ionic species.

Referring to FIG. 2, ionic flow of a four-channel device, according to the invention, is illustrated for a sample pretreatment and suppression in the system illustrated in FIGS. 3 and 4. FIG. 2 illustrates anion analysis, showing chloride as one of the anions to be separated and sodium hydroxide as the electrolyte of the eluent. Flow through channel 12 is in the sample inject mode of FIG. 3. Eluent, including sodium hydroxide, carries the separated analytes represented by the chloride anion through channel 12. For anion analysis, electrode 24 is positively charged (an anode) and electrode 26 is negatively charged (a cathode). Charged barriers 18, 20, and 22, typically ion exchange membranes, e.g. Nafion®, include exchangeable ions of the same charge as the eluent cations to be suppressed. Note that Nafion is a sulfonated tetrafluoroethylene based fluoropolymer-copolymer. Thus, barriers 18, 20, and 22 include exchangeable cations, e.g., sodium for anion analysis. When a potential is applied between electrodes 24 and 26, the sodium ions flow across barriers 20 and 22 toward cathode 26 to channel 16 and out port 16b to suppress the conductivity of the eluent which flows out port 12b. As illustrated, the pretreated analyte anions (chloride) are shown in acid form exiting port 12b. The function performed in channel 12 is the same as the suppression function performed in the central channel of a conventional electrolytic sample sandwich suppressor such as illustrated in the '098 patent. In channel 14, the sample in the sample stream is pretreated prior to loading of sample retainer 58. A continuous flow of liquid is maintained in all channels, during the loading of sample into sample retainer 58 in FIG. 3 and during sample injection into chromatographic column 40, in the injection position of FIG. 4.

Referring again to FIG. 2, as set forth above, sodium and calcium ions are illustrated as the counter-ions in the sample of opposite charge to the anion analytes to be separated and detected. The sodium and calcium ions flow across barrier 22 into channel 16 for removal from the liquid sample prior to sample loading on sample retainer 58. Thus, the sample exiting outlet port 14b, which flows to sample retainer 58, is in acidic form.

In the past, sample pretreatment has been performed using a suppressor-like device, similar to that of the '098 patent. However, there are significant advantages in performing sample pretreatment and suppression in a single device as illustrated in FIGS. 2-4. For example, it lowers the overall cost because a single power supply can be used to perform both functions. Also, if the sample is of a type which tends to precipitate when injected into the system, such precipitated samples can get lodged into a chromatographic column. Thus, due to the high pH condition for anion analysis, multivalent cationic species, such as calcium and magnesium, tend to precipitate. By removal of such counter-ions to the analyte ions to be analyzed, the columns are not subject to precipitation. For example, in suppression, due to the acidic nature of the functional groups, the precipitation can be induced at a relatively higher concentration. Also, due to non-precipitating cations, the effective concentration of the precipitating ions is diminished. In effect, by removing the precipitating ions before analysis, the analytical system is free from these ions and analysis proceeds without interruption. This enables use without removal of such ions in a separate device, e.g. an ion exchange cartridge, before analysis.

The following is a summary of the functions of the system for the two positions of valving 36 as illustrated on FIGS. 3 and 4. In a first position, illustrated in FIG. 3, the liquid sample stream can be loaded into sample retainer 58 and is blocked from flow to chromatographic separator 40. In the second position, illustrated in FIG. 4, sample in sample retainer 58 is in fluid communication with column 40 and is carried to column 40 by eluent from eluent generator 32.

The suppression and sample pretreatment device of FIGS. 2-4 is illustrated for analysis of anions in a cation hydroxide or a salt eluent in which the eluent cations are suppressed. The invention is also applicable to the analysis of cations and suppression of electrolyte counter-ions (anions) in an eluent of opposite charge to the cation analytes. In this instance, the polarity of all elements in the device is reversed. Thus, the barriers are positively charged, i.e., and include exchange ions of negative charge, and the polarities of the electrodes are reversed during operation. Suitable eluents for anion analysis include alkali hydroxides, such as sodium hydroxide or potassium hydroxide, and alkali carbonates and bicarbonates. A suitable eluent solutions for cation analysis is methanesulfonic acid (MSA).

Channels 10 and 16 serve multiple functions similar to the outside channels of the prior art three-channel sandwich membrane device illustrated the '098 patent. One function is to provide the flowing stream to remove the eluent counter-ions to the analyte ions and the counter-ions to the analyte ions in the sample ions in the pretreatment channel 14. Although a recycle configuration is shown in the figure, an external regenerant stream could be used for this function.

Figure 7:
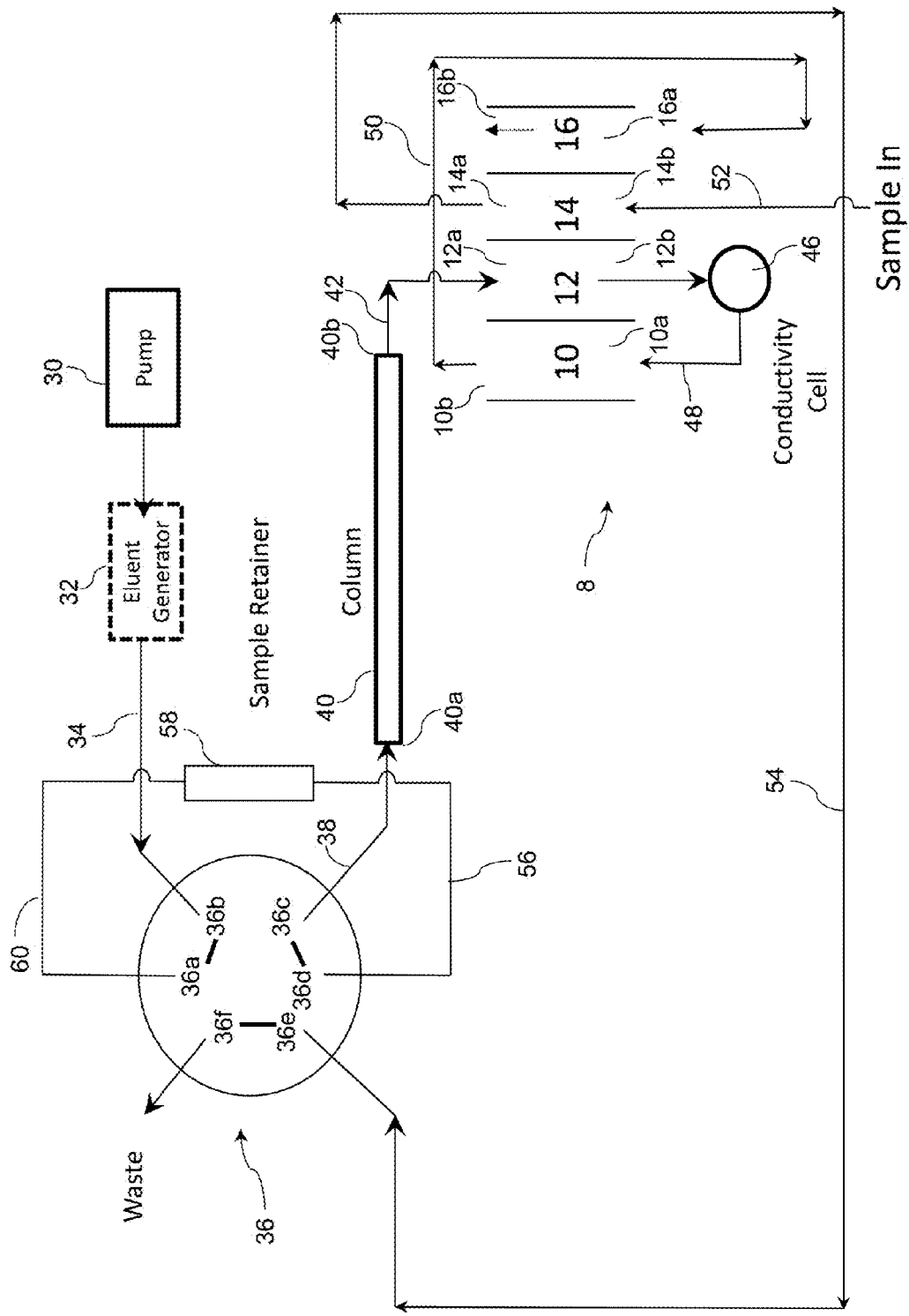
FIG. 7 illustrates the system of FIG. 6 with the valving set to inject the liquid sample in the sample retainer into a chromatography column.
Figure 8:
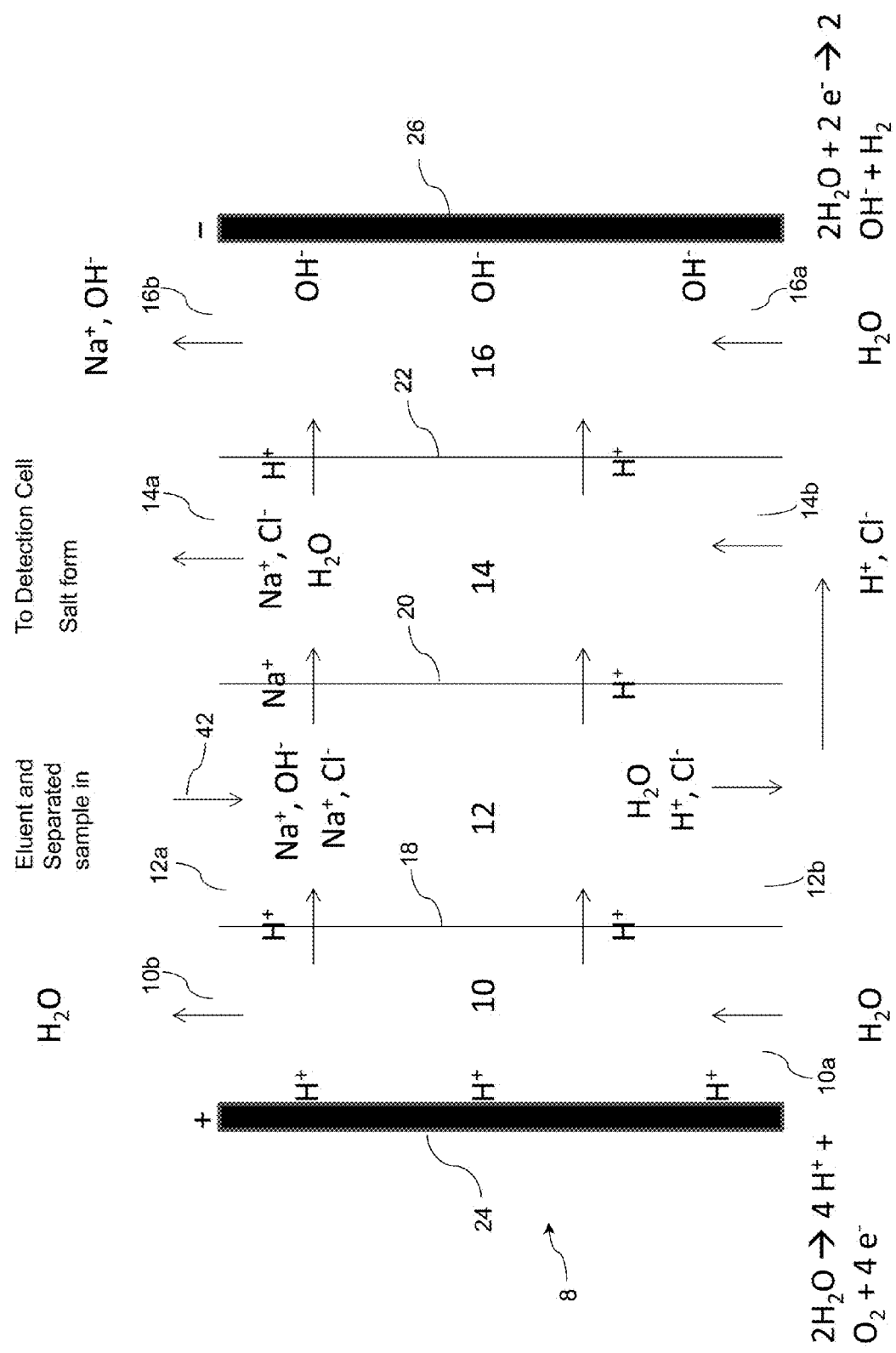
FIG. 8 is a schematic view illustrating ionic flow of the four-channel device used for suppression and conversion of previously separated analyte ions to salt form.

As illustrated in FIGS. 2-4, electrodes 24 and 36 are coextensive with and substantially parallel to barriers 18 and 22, respectively. Also, as illustrated in FIGS. 2-4, flow through suppressor channel 12 and pretreatment channel 14 is concurrent. The illustrated barriers are substantially flat or planar and the channels are substantially flat. However, concentric tubes could be used with one channel at the center and the other channels formed in the external annular spaces as illustrated in FIGS. 7 and 8 of U.S. Pat. No. 6,077,434.

The four-channel device of FIG. 1 may be used in a variety of other systems for analyzing analytes in a liquid sample. Thus, such systems may be used solely for pretreatment or solely for suppression in a suppressed ion chromatography system or both. Also, the invention also encompasses devices with five channels (or more) constructed like the four channel device but with an additional charged barrier for each additional channel.

Figure 5:
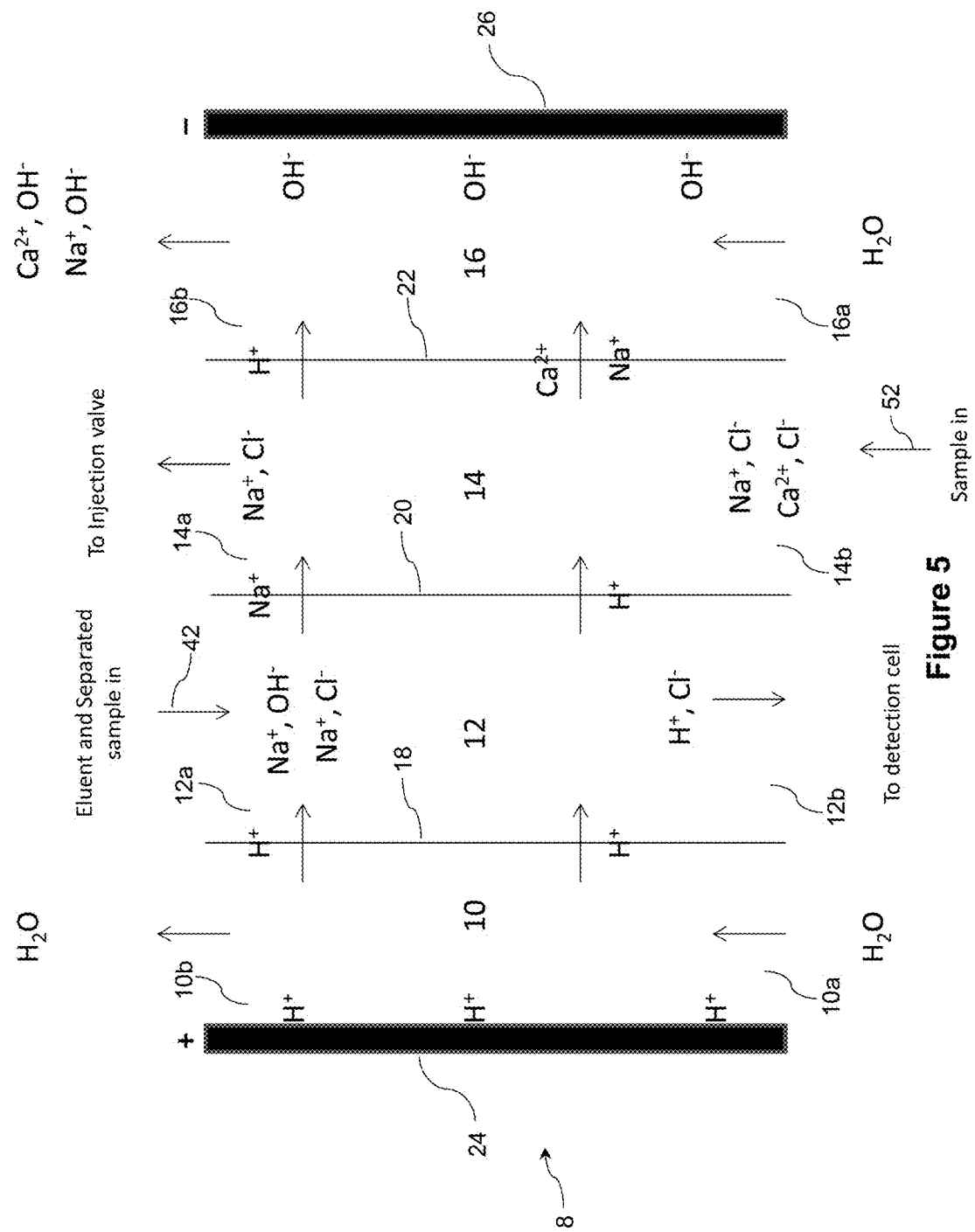
FIG. 5 is a schematic view of a four-channel device for pretreatment of a sample stream containing unseparated analytes and suppression of the eluent illustrating ionic flow.
Figure 6:
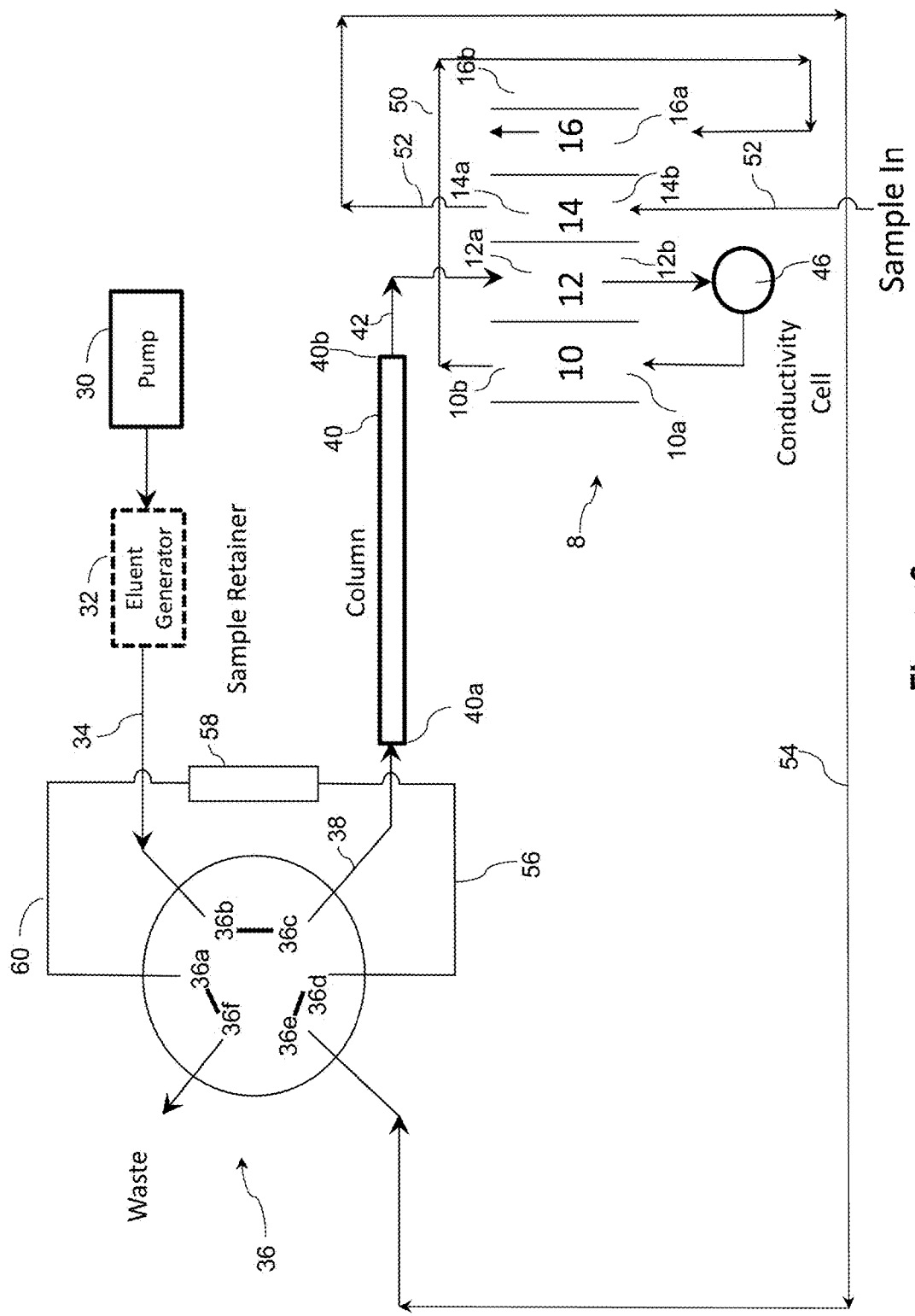
FIG. 6 is a schematic view of a system using the device of FIG. 5 with the valving set to load the sample into a sample retainer.

FIGS. 5-7 illustrate the four-channel device of FIG. 1, in a system in which the sample is converted to salt form prior to flow to sample retainer 58, instead of acid form for anion analysis, as in FIGS. 2-4. The principal difference between the embodiments of FIGS. 2-4 and that of FIGS. 5-7 is that, instead of concurrent flow as in the former embodiment, flow through suppressor channel 12 is in countercurrent to that of flow through sample pretreatment channel 14 in the latter embodiment. Like parts will be designated with like numbers for the embodiments of FIGS. 2-4 and FIGS. 5-7.

Ports described as inlets and outlets herein are ports which can serve the function of an inlet or an outlet. Thus, the same designations for these ports will be used even if the flow may be reversed so that an inlet port may be an outlet port and vice versa for subsequent embodiments.

Referring to FIG. 6, valving 36 is set in the first position for sample loading as in FIG. 3. Flow from pump 30 through column 40, channel 12, detector 46, channel 10 and channel 16 are the same as for FIG. 3. The principal difference is that the sample flowing through channel 14 flows from port 14b to port 14a, so that port 14a is an outlet and port 14b is an inlet, whereas in FIG. 3, port 14a is an inlet and port 14b is an outlet. Thus, flow through channel 12 is countercurrent to flow through channel 14, as illustrated in FIG. 6. The stream flowing out port 14b flows in line 54 to sample retainer 58, as illustrated in FIG. 3.

Referring to FIG. 7, the system is the same for sample injection as for the embodiment of FIG. 4 except that, as in FIG. 6, sample flow through sample pretreatment channel 14 is countercurrent to flow through suppressor channel 12.

FIG. 5 is a schematic representation of ion flow in of the device of FIGS. 6 and 7, illustrating a countercurrent flow in channels 12 and 14. As illustrated in FIG. 5, the sample flowing into port 14b is converted into a salt as it exits port 14a. As illustrated, the sample flowing in line 52 into port 14b includes sodium and calcium counter-ions, which are removed from channel 14 and flow across barrier 22 in the form of a cation exchange membrane. However, near exit port 14a, the eluent entering channel 12 through inlet 12a, adjacent to the exit end of channel 14, still includes a high concentration of cations because suppression is just beginning. Thus, for sodium hydroxide electrolyte in the eluent, the sodium ions in the eluent flowing into port 12a, are illustrated as flowing across cation exchange barrier 20 into pretreatment channel 14, and the analyte ions, illustrated as chloride, form sodium chloride salt which exits port 14a for loading into sample retainer 58. Thus, the sample anions exiting port 14a are in the salt form of the electrolyte in the eluent.

An advantage of converting to the salt form by countercurrent flow in channels 12 and 14 can be illustrated by analysis of cations. If flow were concurrent as in FIGS. 2-4, the calcium hydroxide would be the post-suppressor product, which tends to precipitate at high concentrations. By using countercurrent flow as in FIGS. 5-7, the sample can be injected into separator 40 as a salt, such as calcium methane sulfonate, which does not precipitate.

Figure 9:
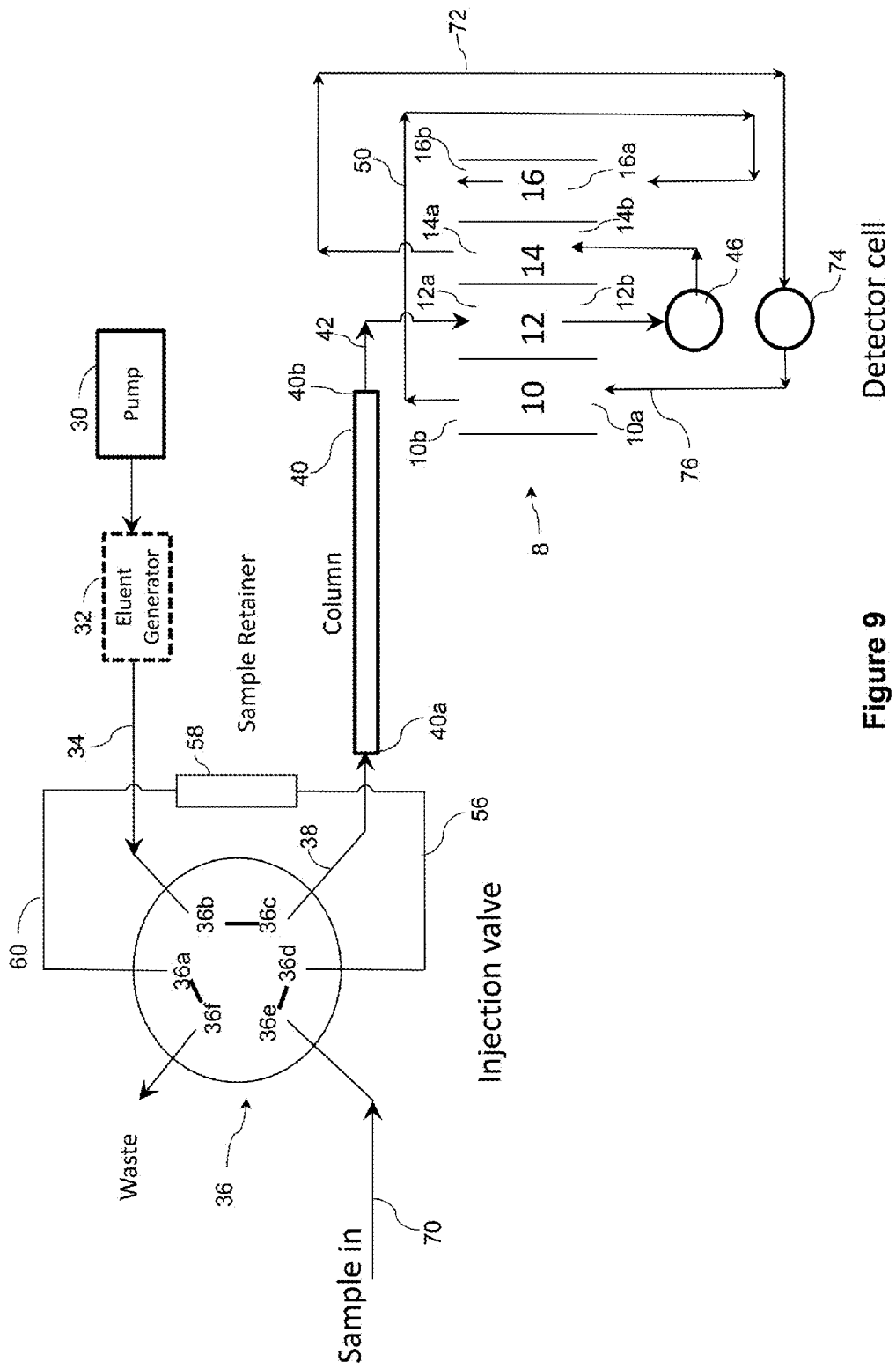
FIG. 9 is a schematic view of a system using the device of FIG. 8, with the valving set to load the unseparated sample into a sample retainer.
Figure 10:
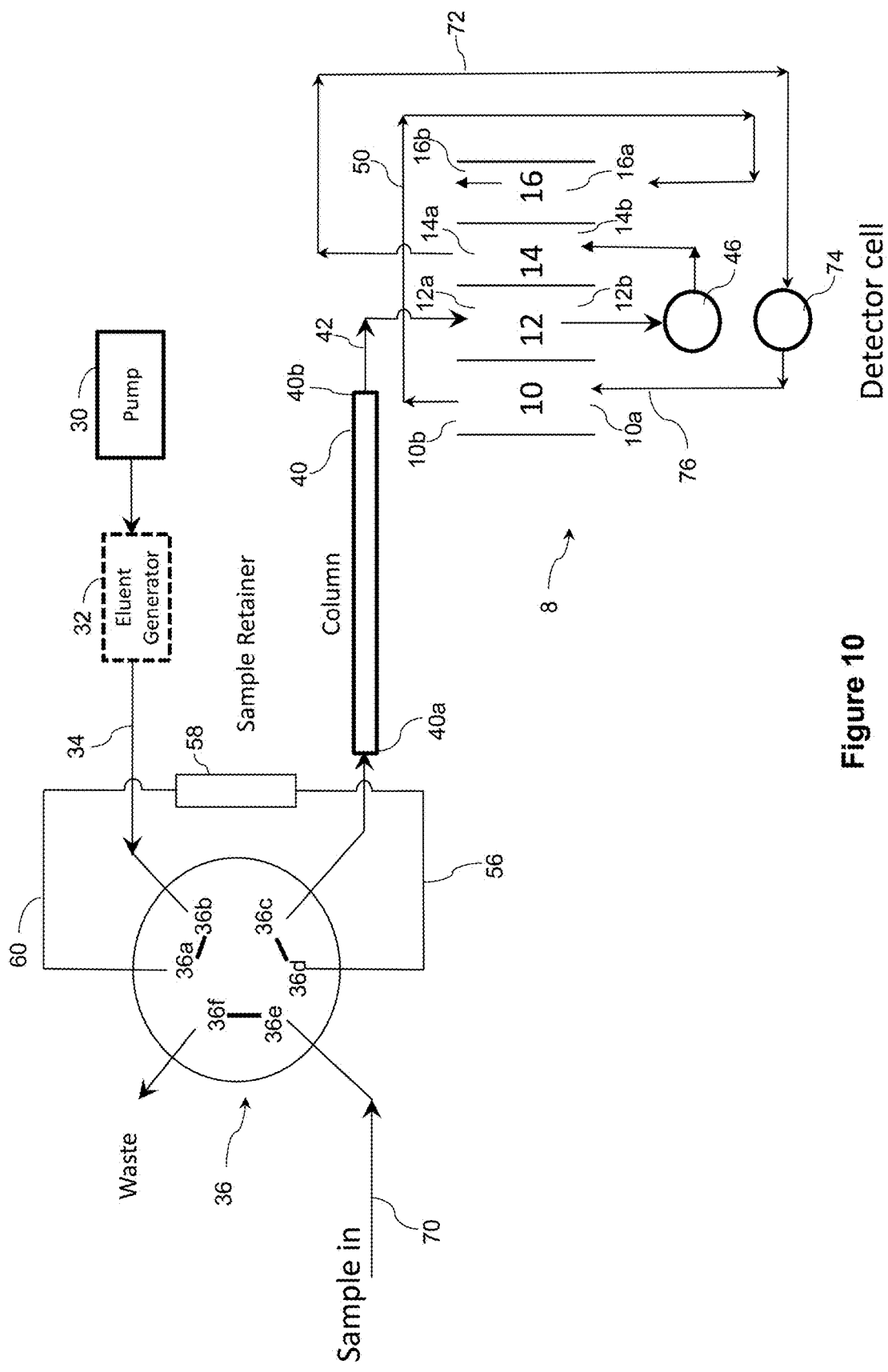
FIG. 10 illustrates the system of FIG. 9, with the valving set to inject the liquid sample in the sample retainer into a chromatographic column.

Referring to FIGS. 8-10, the device of FIG. 1 is used for salt conversion after suppression without sample pretreatment. Like parts be designated with like numbers as for FIGS. 2-8.

FIG. 9 illustrates valving 36 in a sample loading position in which sample is loaded into sample retainer 58. Here the liquid sample is not pretreated in four-channel device 8. Instead, the liquid sample stream flows in line 70 through ports 36e and 36d to load sample retainer 58 and from there through line 60, ports 36a and 36f to waste. Liquid streams flow continuously through the system. Eluent is pumped through line 34, ports 36b and 36c through column 40 and through inlet port 12a through channel 12, detector 46, and then through port 14b channel 14, outlet port 14a, line 72, a second detector 74, line 76 to inlet port 10a through channel 10, outlet port 10b, line 50, into inlet port 16a of channel 16 and outlet port 16b to waste. Flow through channels 12 and 14 is countercurrent.

FIG. 10 illustrates the system of FIG. 9 with valving 36 set to inject a sample into column 40. The liquid sample stream in line 70 flows through ports 36e and 36f to waste. Eluent in line 34 flows from eluent generator 32 through ports 36b and 36a, line 60, to carry sample in sample retainer 58 to ports 36d and 36c, line 38 to column 40, line 42 to inlet port 12a, channel 12, to outlet port 12b detector 46, inlet port 14b, channel 14, outlet port 14a through line 72 and past a second detector 74 for detection. The outlet from detector 74 flows through inlet port 10a, channel 10, outlet port 10b in line 50 into port 16a, channel 16 and out port 16b to waste. Here again, flow through channel 12 is countercurrent to flow through channel 14.

In the system of FIG. 10, suppression is performed in channel 12 for detection in detector 46 in a similar manner to that of a conventional sandwich suppressor such as is set forth in the above '098 patent. Thus, the anion or cation analytes are in acid or base form, respectively. Flow from detector 46 is back through channel 14 in a countercurrent direction and the sample analytes are converted to salt form for detection in detector 74 as illustrated in the schematic diagram of ion flow of FIG. 8. Here, when the eluent is near the inlet of channel 12, suppression is in an early stage and so the eluent counter-ion to the sample ion is still highly concentrated. Such counter-ions, sodium as illustrated, flow across membrane 20. The solution exiting channel 12 through port 12b is detected by detector 46 and then is recycled back through inlet port 14b to channel 14 and is converted to salt form by the sodium ions flowing across membrane 20 near the inlet of channel 12 to convert the eluent, containing separated sample ions, illustrated as chloride, in channel 14 to the salt form. Thus, as illustrated, chloride is converted to sodium chloride form.

In this embodiment the suppressed and salt forms may be detected by detectors 46 and 74, respectively. To illustrate the advantage of this, weak base such as ammonium ion response gives a non-linear fit with concentration when performing suppressed chromatography, but by combining with a salt converter, a linear fit can be achieved. Thus, the weakly dissociated species can be analyzed effectively along with strongly dissociated species by the present invention.

Other embodiments of the invention are methods for treating a sample stream in the above electrolytic device in which the sample stream flows into the second channel inlet through the second channel and out the second channel outlet, and aqueous liquid streams flow through the first, third and fourth channels ("the aqueous liquid stream embodiments").

Figure 11:
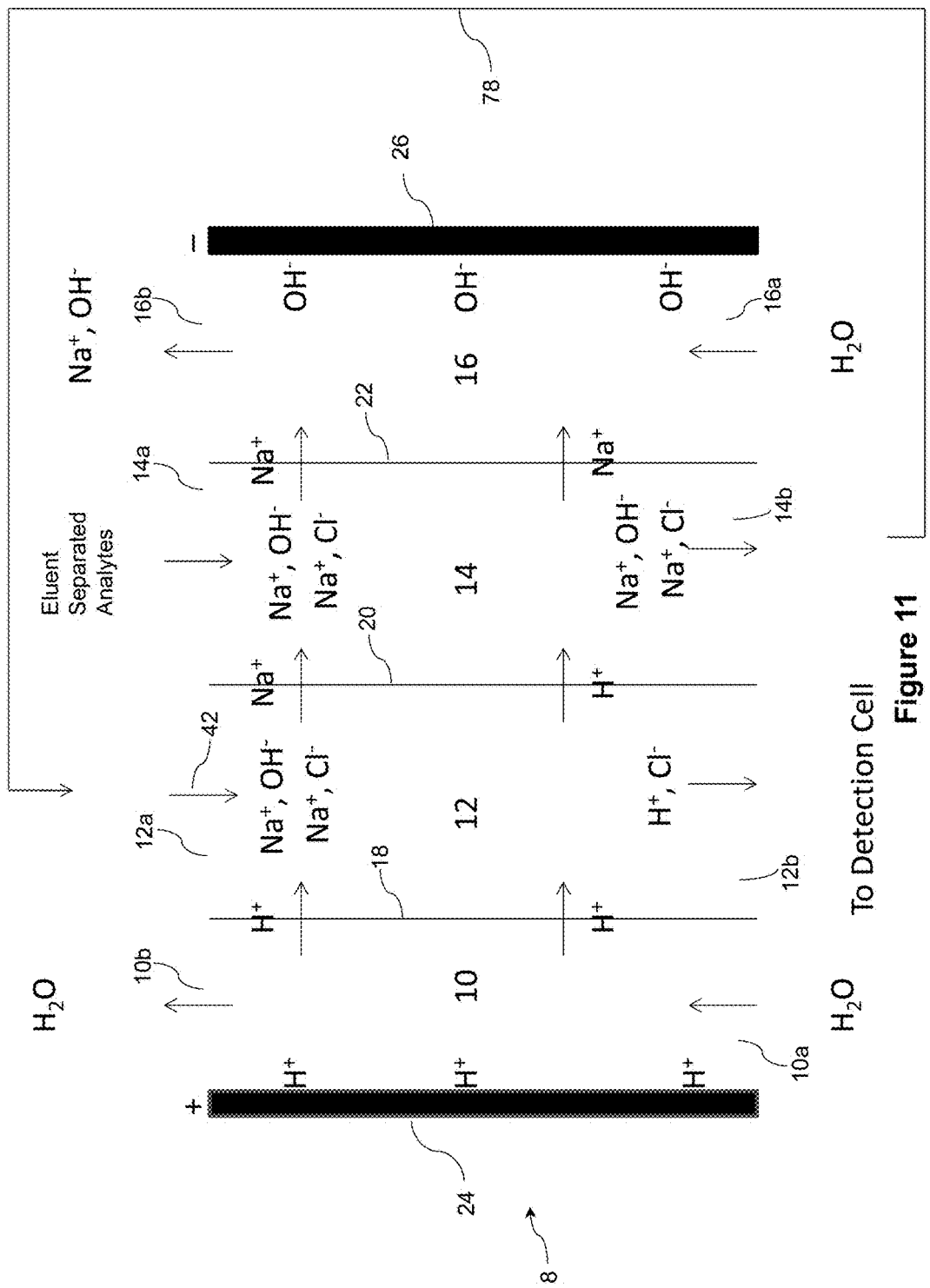
FIG. 11 is a schematic expanded view of the four-channel device used for double-pass suppression illustrating ionic flow.
Figure 12:
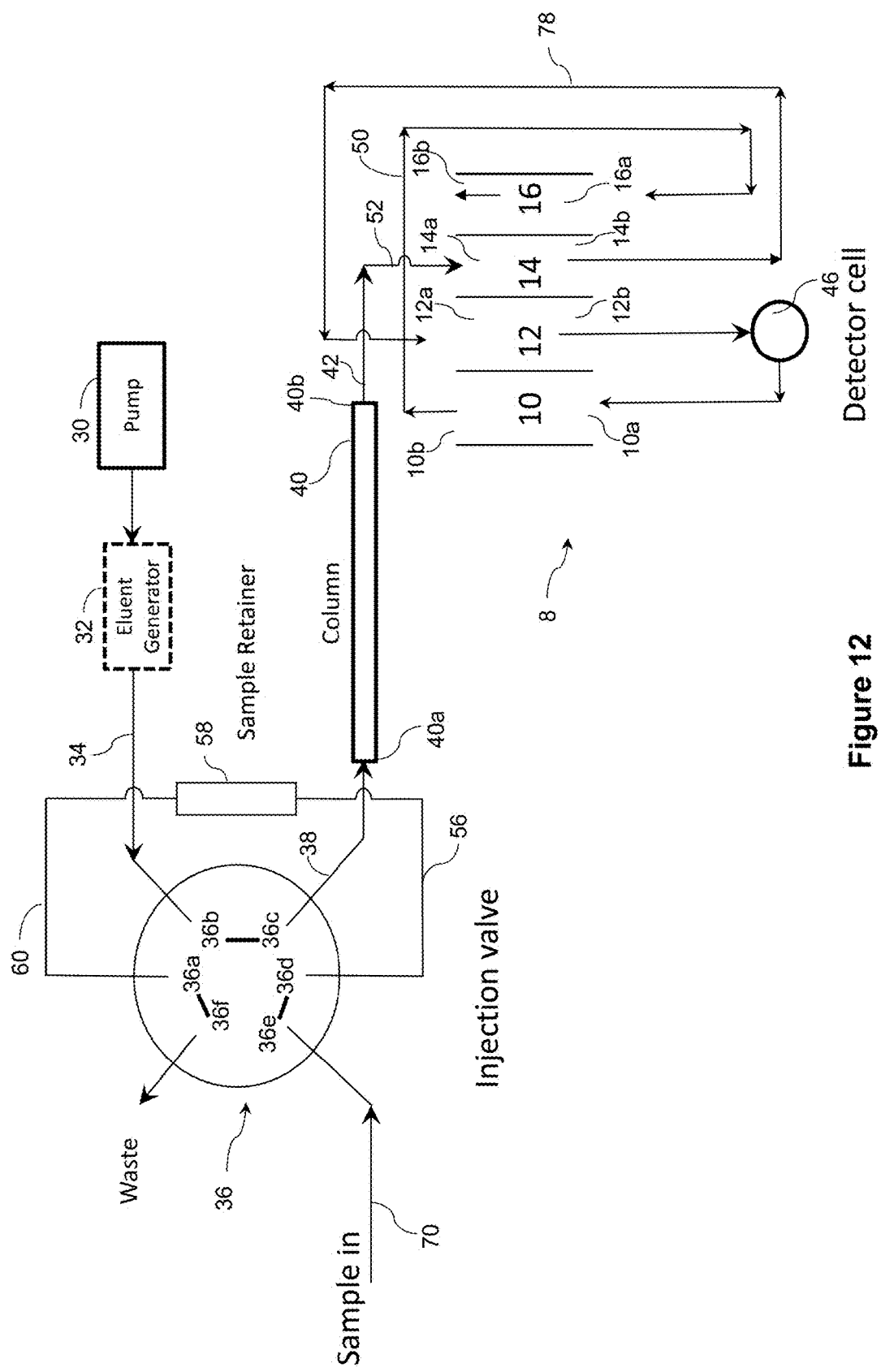
FIG. 12 is a schematic view of a system using the device of FIG. 11, with the valving set to load the sample liquid containing unseparated sample analytes in a sample retainer.
Figure 13:
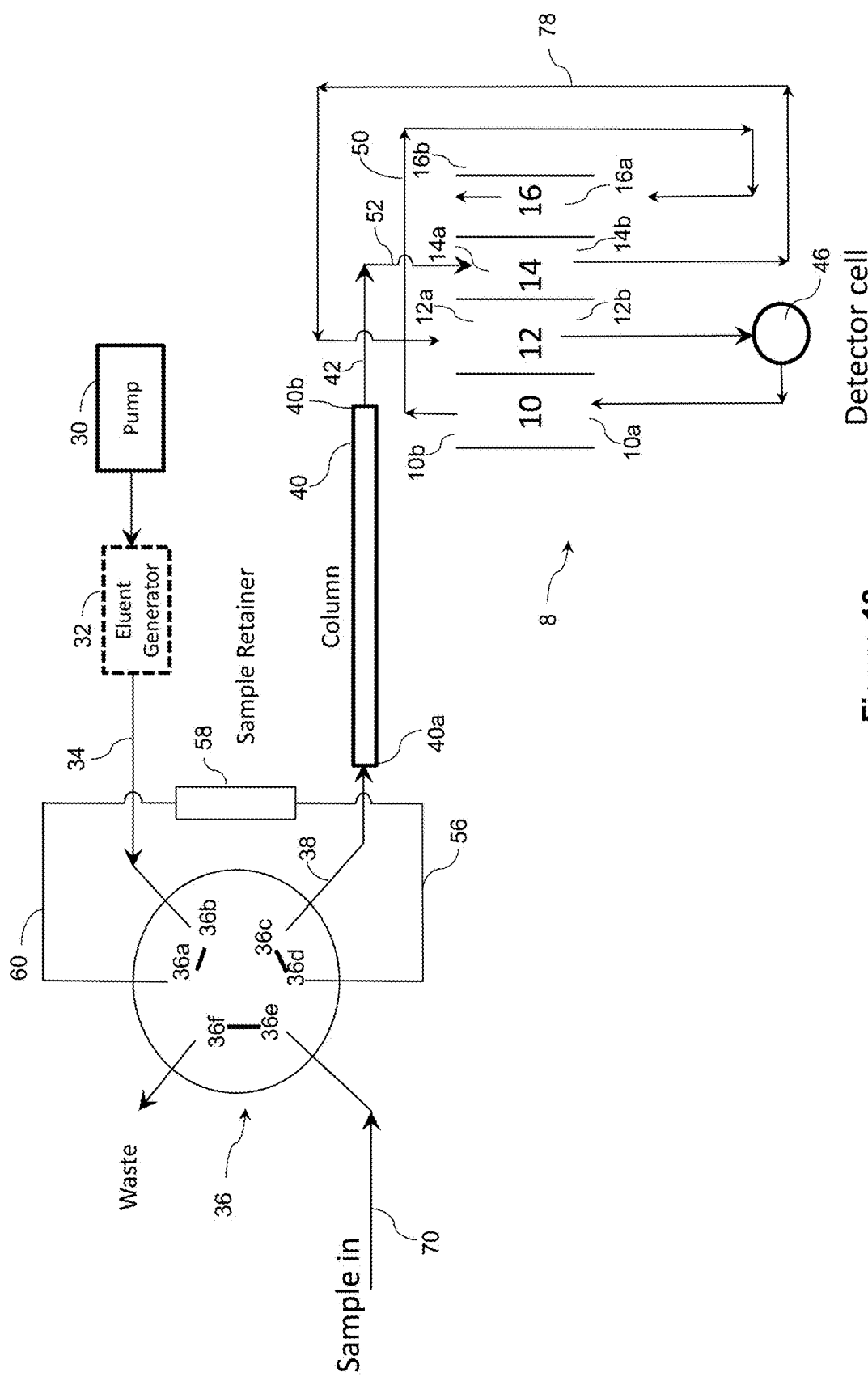
FIG. 13 is a schematic view of a system using the device of FIG. 12, with the valving set to inject the liquid sample in the sample retainer into a chromatography column.

FIGS. 11-13 illustrate one of the aqueous liquid stream embodiments, in which the apparatus of FIGS. 8-10 is used to provide a double pass (i.e. two passes) of the eluent and separated sample analytes through the four-channel device 8 for suppression. Here, the aqueous liquid stream in the third channel is the stream flowing from the second channel outlet to the third channel inlet. This embodiment is used for suppression and includes no sample pretreatment. Like parts will be used to designate like numbers as the embodiments of FIGS. 8-10.

In FIG. 12, valving 36 is illustrated for loading of sample into sample retainer 58. The sample stream flows in line 70 through ports 36e and 36d, line 56 sample retainer 58, line 60, ports 36a and 36f to waste. To maintain flow through device 8, eluent is pumped from eluent generator 32 by pump 30 through ports 36b and 36c through column 40 to inlet port 14a of channel 14, out outlet port 14b to recycle in line 78 to inlet port 12a through channel 12 and out port 12b. From there, the stream flows through detector 46, port 10a, channel 10, and outlet port 10b through inlet port 16a of channel 16 and outlet port 16b to waste.

Referring to FIG. 13, the apparatus of FIG. 12 is used for suppressed ion chromatography in which sample is injected into column 40. Here, the sample stream flowing in line 70 flows through ports 36e and 36f to waste. Eluent from eluent generator 32 is pumped by pump 30 in line 34 through ports 36b and 36a through line 60, to carry sample in sample retainer 58 to line 56, and ports 36d and 36c to column 40 and from there to inlet port 14a and through channel 14. Solution exiting channel 14 flows through port 14b, line 78 through inlet port 12a through channel 12 to detector 46. From there, the solution flows through channel 10 and then through channel 16 to waste. During the sample injection mode, a first suppression step is performed in channel 14 and a second suppression step is performed in channel 12 prior to detection by detector 46.

Referring to FIG. 11, the ion flow of this double pass embodiment is illustrated. Flow through suppression channels 12 and 14 is concurrent. Thus, suppression begins at the inlet section adjacent port 12a for channel 12 and port 14a for channel 14. The eluent counter ion in the solution exiting port 14b is partially suppressed and so is illustrated in salt form although part of the eluent counter-ion has been suppressed (removed). The doubly suppressed sample in acid or base form exits port 12b for flow to detector 46.

By use of the double pass flow system of FIGS. 11-13, the capacity of the suppressor device is significantly enhanced because of the additional residence time in the suppressor device. Also, the wattage per unit area of an eluent screen in a suppressor channel is diminished, leading to lowered waste and improved lifetime of the suppressor device.

Figure 14:
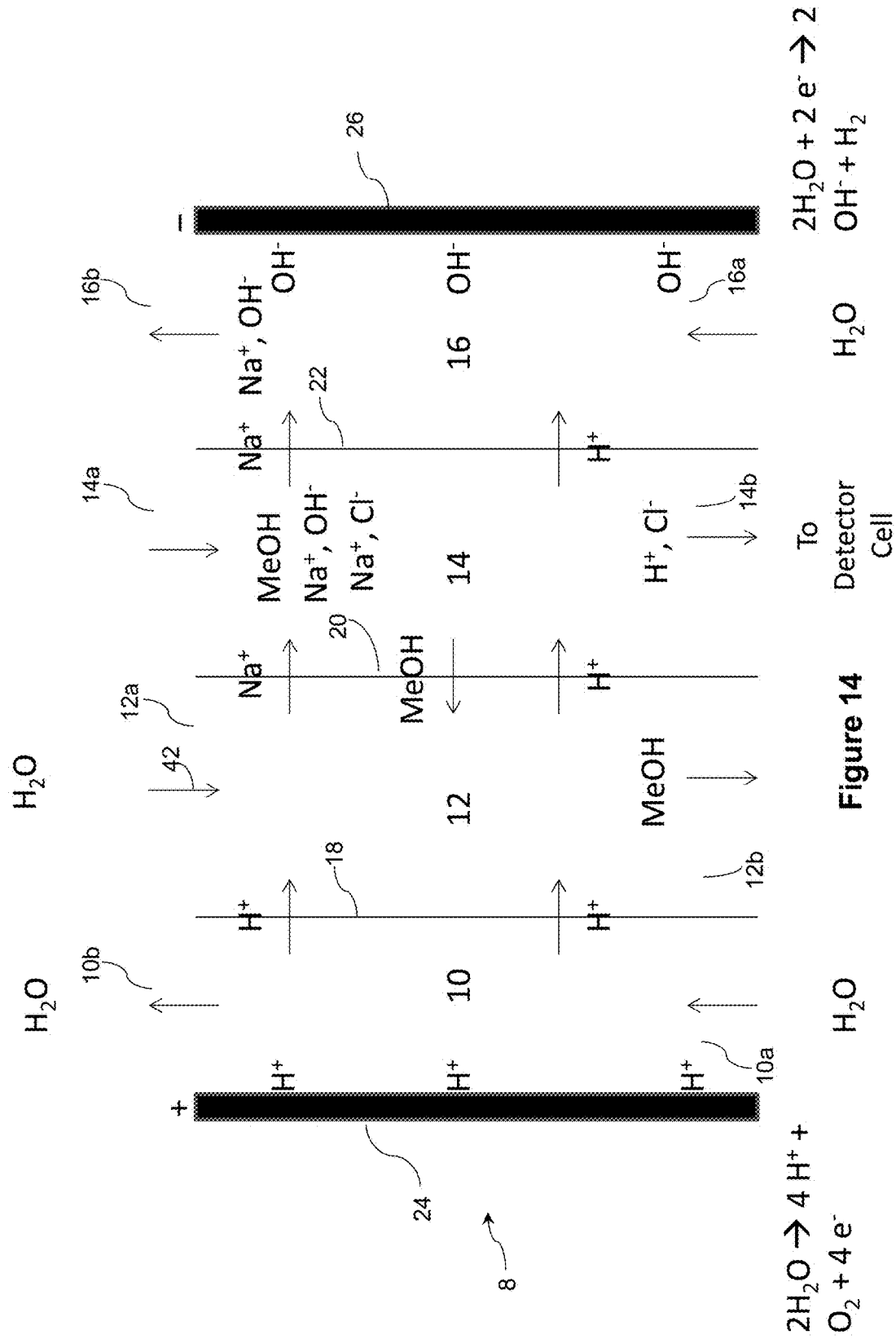
FIG. 14 is a schematic view of ion flow for using the four-channel device for suppressing a solvent-containing eluent.

FIG. 14 illustrates ion flow of the system of FIGS. 12 and 13 used in a solvent application. Flow through suppression channel 14 is concurrent. Thus, suppression begins at the inlet section adjacent port 14a for channel 14 similar to a standard suppressor. The sodium ion which is the counter ion to the eluent is removed via barrier 22 and is sent towards the cathode 26 by the applied potential. Hydronium is transported from the anode 24 via barriers 18 and 20 and enters channel 14. The solvent in the eluent diffuses towards channel 12 as illustrated by transport of methanol represented here as MeOH. The solvent MeOH is diluted by the deionized water flow in channel 12 and is routed to waste. The flow in channel 12 is concurrent to the eluent channel flow in channel 14. In general, this embodiment shows improved compatibility with the solvent. Typical solvents used for ion chromatography can be used in this mode such as methanol, acetonitrile, isopropyl alcohol and the like. The key benefit of this mode is that the alcohol is not directly exposed to the anode where oxidation would result in other species that would be detrimental for chromatography. For example methanol can be oxidized to formate which in the weak formic acid form can permeate the membranes. Since in this mode there is an extra channel 12 between the anode 24 and the suppressing channel 14 the diffusion of any oxidized species is considerably diminished.

The above aqueous liquid stream embodiments have described a dual function integrated into four-channel device. However, in methods of using such a device, a user has the option to use only one of the two functions where an aqueous liquid stream flows through the particular chamber that is not performing its function. For example, an integrated pre-treatment/suppressor device may be used such that only the sample pre-treatment channel is active or that only the suppressor channel is active. More particularly, the integrated pre-treatment/suppressor device may have only the pretreatment channel active where an independent aqueous stream is flowed through the second channel 12 (suppressor channel) instead of eluent and separated sample. Similarly, the integrated pre-treatment/suppressor device may have only the suppressor channel active where an independent aqueous stream is flowed through the third channel 14 (sample pretreatment channel) instead of unseparated sample.

In another example, an integrated suppressor/salt generator device may be used such that only the suppressor channel is active or that only the salt generator channel is active. More particularly, the integrated suppressor/salt generator device may have only the suppressor channel active where an independent aqueous stream is flowed through the third channel 14 (salt generator channel) instead of a suppressed sample stream. Similarly, the integrated suppressor/salt generator device may have only the salt generator channel active where an independent aqueous stream is flowed through the second channel 12 (suppressor channel) instead of eluent and separated sample.

In yet another example, an integrated double suppressor device may be used such that only one suppressor channel is active or that both suppressor channels are active. More particularly, the integrated double suppressor device may have only one suppressor channel active where an independent aqueous stream is flowed through the third channel 14 (second suppressor channel) instead of a suppressed sample stream. The output from the one suppressor channel can be in fluid communication with a detector.

In another aqueous liquid stream embodiment of a four-channel device, a liquid sample stream containing unseparated analytes ion and counterions to the analyte ions can be pretreated in one of the channels. A detector may be placed at the outlet of the pretreatment channel to monitor the purity of the pretreated sample stream. More particularly, the liquid sample stream can be pretreated in the pretreatment channel such as, for example, the third channel as described in FIGS. 2, 5, and 14. Suitably, an aqueous liquid stream from an independent source may be used as the aqueous liquid stream flowing through one or all of the first, second, and fourth channel.

By isolating the regenerant channel 10 from the solvent in channel 14 via use of an additional channel 12 which has deionized water, migration of the solvent to the anode 24 is minimized. This means any oxidizing reactions at the anode are also minimized. The net effect is that solvent compatibility of the suppressor is improved without compromising suppression. It should be noted that the independent deionized water flow in the three channels 10, 12 and 16 is the most preferred format. Depending on the extent of solvent diffusion, the waste from one of the channels could be the source of the deionized water of the other channel.

In order to illustrate the present invention, the following non-limiting examples of its practice are provided.

Example 1

Pretreatment and Suppression

Figure 15:
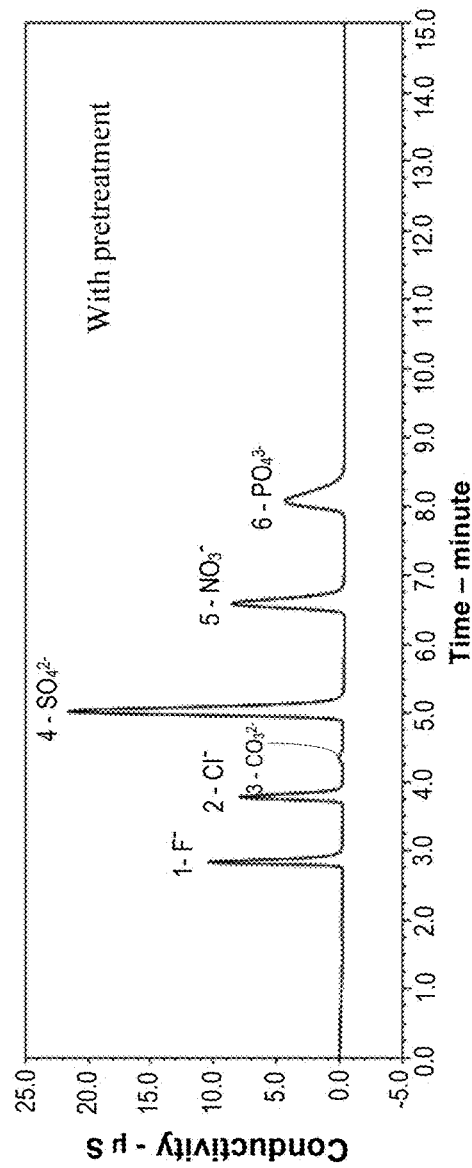
FIG. 15 is a chromatogram illustrating anion analysis using sample pretreatment and suppression in accordance with FIGS. 1 and 2.
Figure 16:
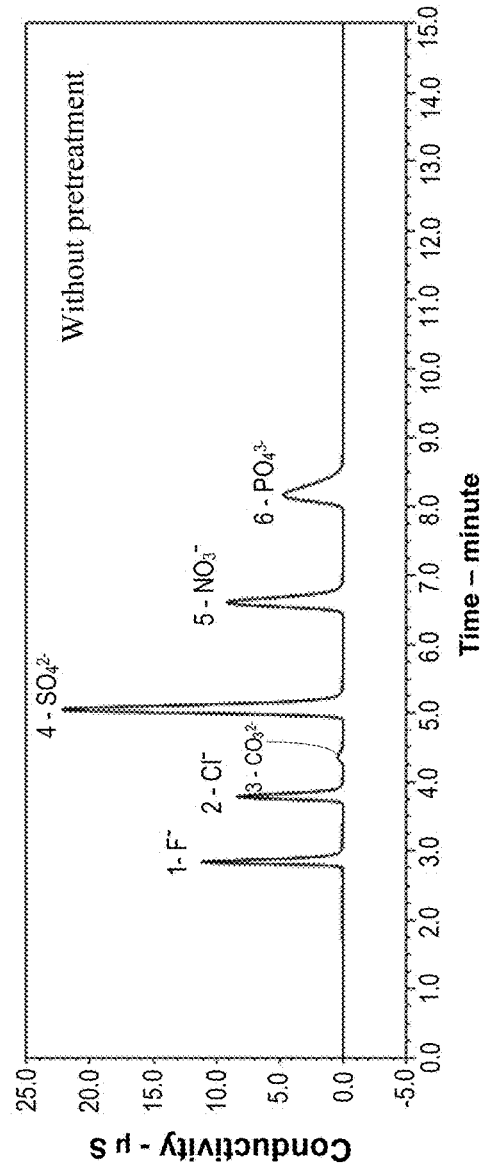
FIG. 16 is a chromatogram illustrating anion analysis using suppression without sample pretreatment.

A device as illustrated in FIG. 1 was assembled for the anion analysis and was used to pretreat the sample and suppress the cation counter-ions in the anion sample prior to injection into the column as illustrated in FIG. 2. The assembly was similar to the Dionex commercial three-channel suppressor model ASRS 300 (4 mm), except it includes three ion exchange membranes defining four channels. A five anion standard was used in this application after diluting this tenfold. The five anions in the standard were fluoride (2.0 ppm), chloride (3.0 ppm), sulfate (15 ppm), nitrate (10 ppm) and phosphate (15 ppm). The standard was delivered to the sample polishing or pretreatment channel by an auto sampler (Dionex AS40). Channel 14a of FIG. 2 was used for the sample pretreatment aspect. An IonPac® AS18 chromatography column was used for the separation at a concentration of 32 mM KOH. The flow rate was 1 mL/min and the sample loop had a 25 µL volume. The applied current was the recommended current of 80 mA and complete suppression of the eluent was achieved with good separation of all peaks. The performance of the unit with and without sample pretreatment was evaluated to ensure that the unit was capable of pursuing sample pretreatment applications as well as the suppression applications and the results showed a comparable performance in peak area as shown in FIGS. 15-16 and Table 1. Note that peak 3 in FIGS. 15-16 represents a small impurity of carbonate. Further the results also validated that the chromatographic properties of the peaks such as peak shape (peak efficiency, asymmetry) are preserved and are not affected by the added new function of the device. These results demonstrate that the suppressor unit of the present invention would allow sample pretreatment in conjunction with suppression for critical applications.

TABLE 1

| Peak Name | PeakArea Control | PeakArea with sample pretreatment |
| --- | --- | --- |
| 1 - Fluoride | 0.9096 | 0.8701 |
| 2 - Chloride | 0.7967 | 0.7714 |
| 4 - Sulfate | 3.0131 | 2.9383 |
| 5 - Nitrate | 1.4923 | 1.4630 |
| 6 - Phosphate | 1.3110 | 1.2620 |

Example 2

Double Pass

Figure 17:
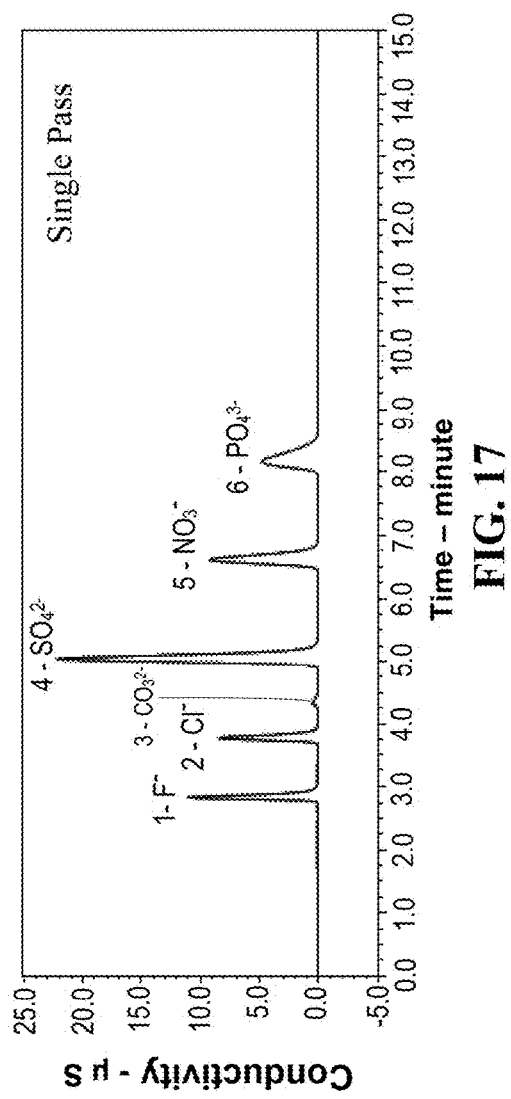
FIG. 17 is a chromatogram illustrating anion analysis using suppression with a single pass through a channel.
Figure 18:
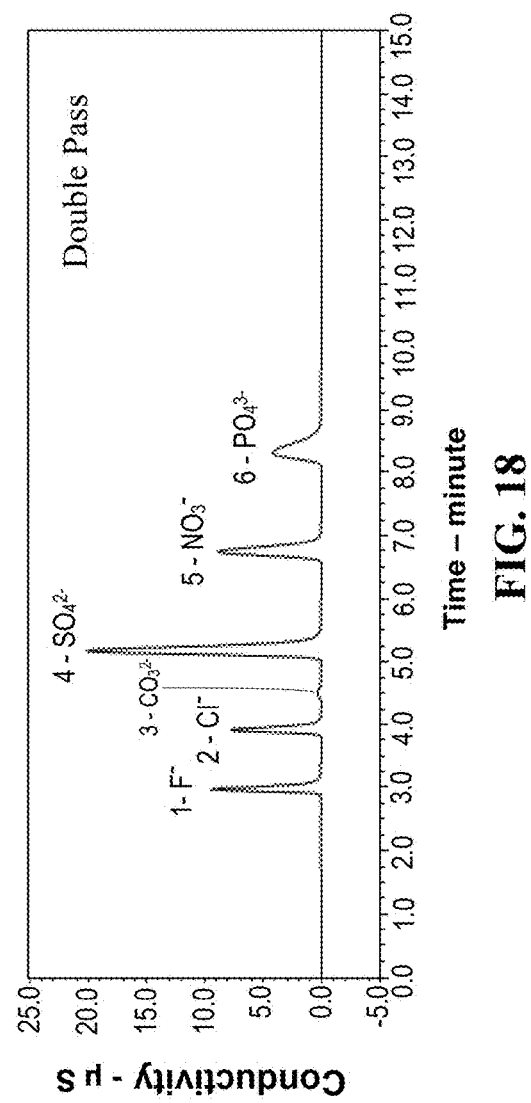
FIG. 18 is a chromatogram illustrating anion analysis using double pass suppression in accordance with FIGS. 11-13.

A setup of the device of FIG. 1 was used to test the double-pass embodiment for anion analysis of FIG. 11-13. The conditions were identical to Example 1. Here the eluent was routed through channel 14 for a second time (double pass) and compared with the performance when the eluent was only routed through the eluent channel (single pass). Nearly identical performance in peak response was observed for the single-pass and double pass embodiments demonstrating the utility of this approach as shown in FIGS. 17-18 and Table 2.

TABLE 2

| Peak Name | PeakArea Single Pass | PeakArea Double Pass |
| --- | --- | --- |
| 1 - Fluoride | 0.9096 | 0.9097 |
| 2 - Chloride | 0.7967 | 0.7977 |
| 4 - Sulfate | 3.0131 | 3.0022 |
| 5 - Nitrate | 1.4923 | 1.4948 |
| 6 - Phosphate | 1.311 | 1.2554 |

The results indicated that the device of the present invention can suppress by a double pass approach. Further the results also validated that the chromatographic properties of the peaks such as peak shape (peak efficiency, asymmetry) are preserved and are not affected by the added new function of the device. The double pass approach allows improved dynamic capacity for the suppression function. This means a higher eluent strength can be suppressed by the present invention without compromising significantly on the peak shapes. For high eluent strength the devices of the prior art would require two or more suppressors in series. In the present approach by using a single device the costs are minimized and higher eluent strength can be suppressed.

Example 3

Pretreatment and Suppression

Figure 19:
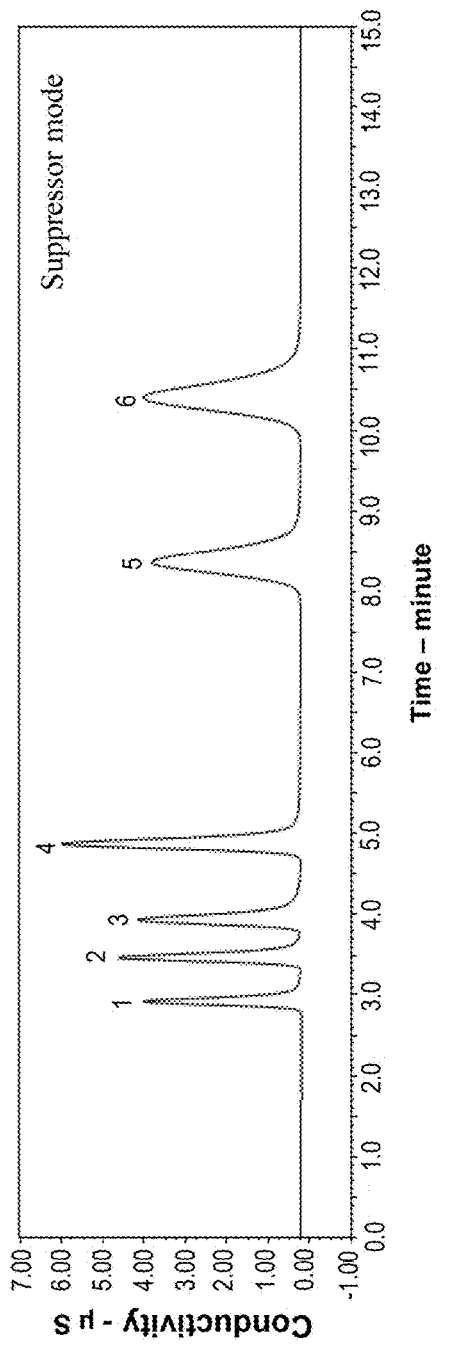
FIG. 19 is a chromatogram illustrating cation analysis using suppression without sample pretreatment.
Figure 20:
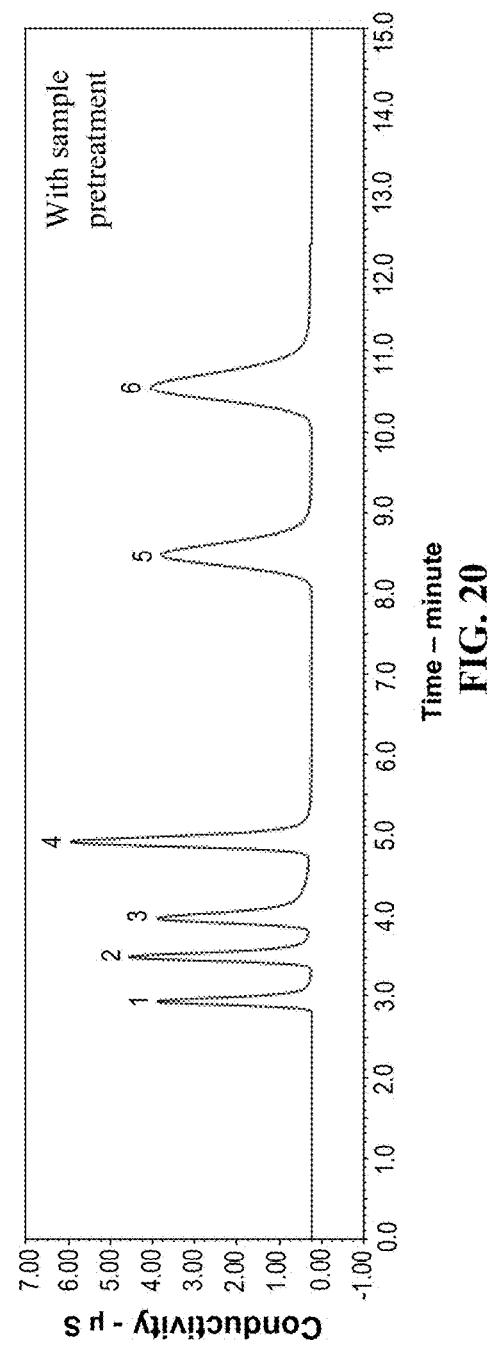
FIG. 20 is a chromatogram illustrating cation analysis using sample pretreatment and suppression in accordance with FIG. 1.

This example illustrates sample pretreatment and suppression in a four-channel device. The device of FIG. 1 was assembled for the CSRS format (4 mm, cation sample) and was used to suppress the anion counter ions to the sample prior to injection into the column. A six cation standard was used in this application, which contained lithium (0.5 ppm), sodium (2.0 ppm), ammonium (2.5 ppm), potassium (5.0 ppm), magnesium (2.5 ppm), and calcium (5.0 ppm). The channel close to the anode was used for the sample pretreatment aspect. An IonPac CS12A column was used for the separation at a concentration of 20 mM MSA. The flow rate was 1 mL/min and the column temperature was 30° C. The applied current was the recommended current of 59 mA and complete suppression of the eluent was achieved with good separation of all peaks. The performance of the unit with and without sample pretreatment showed a comparable performance in peak area as shown in FIGS. 19-20 and Table 3. The performance of the unit with and without sample pretreatment was evaluated to ensure that the unit was capable of pursuing sample pretreatment applications as well as the suppression applications and the results showed a comparable performance in peak area. Further the results also validated that the chromatographic properties of the peaks such as peak shape (peak efficiency, asymmetry) are preserved and are not affected by the added new function of the device. These results demonstrate that the suppressor unit of the present invention would allow sample pretreatment in conjunction with suppression for selected applications.

TABLE 3

| Peak Name | PeakArea Control | PeakArea with sample pretreatment |
|---|---|---|
| 1 - Lithium | 0.415 | 0.423 |
| 2 - Sodium | 0.525 | 0.536 |
| 3 - Ammonium | 0.594 | 0.6 |
| 4 - Potassium | 0.894 | 0.905 |
| 5 - Magnesium | 1.272 | 1.281 |
| 6 - Calcium | 1.592 | 1.631 |

Example 4

Double Pass

In this experiment, the system of FIG. 1 was assembled for a double pass as in FIGS. 11-13 for the CSRS format (cation analytes) and was used to suppress various concentrations of methanesulfonic acid eluent. The suppressor was able to easily suppress 170 mM of MSA at a flow rate of 1 mL/min at a set current of 500 mA. The standard suppressor was able to suppress a maximum capacity of 110 mM of MSA at 1 mL/min at a set current of 330 mA. By using two channels, the suppressor of the present invention could suppress a higher concentration of the eluent. It should be noted that the power supply in use had a maximum current of 500 mA hence higher concentrations were not tested.

Example 5

Figure 21:
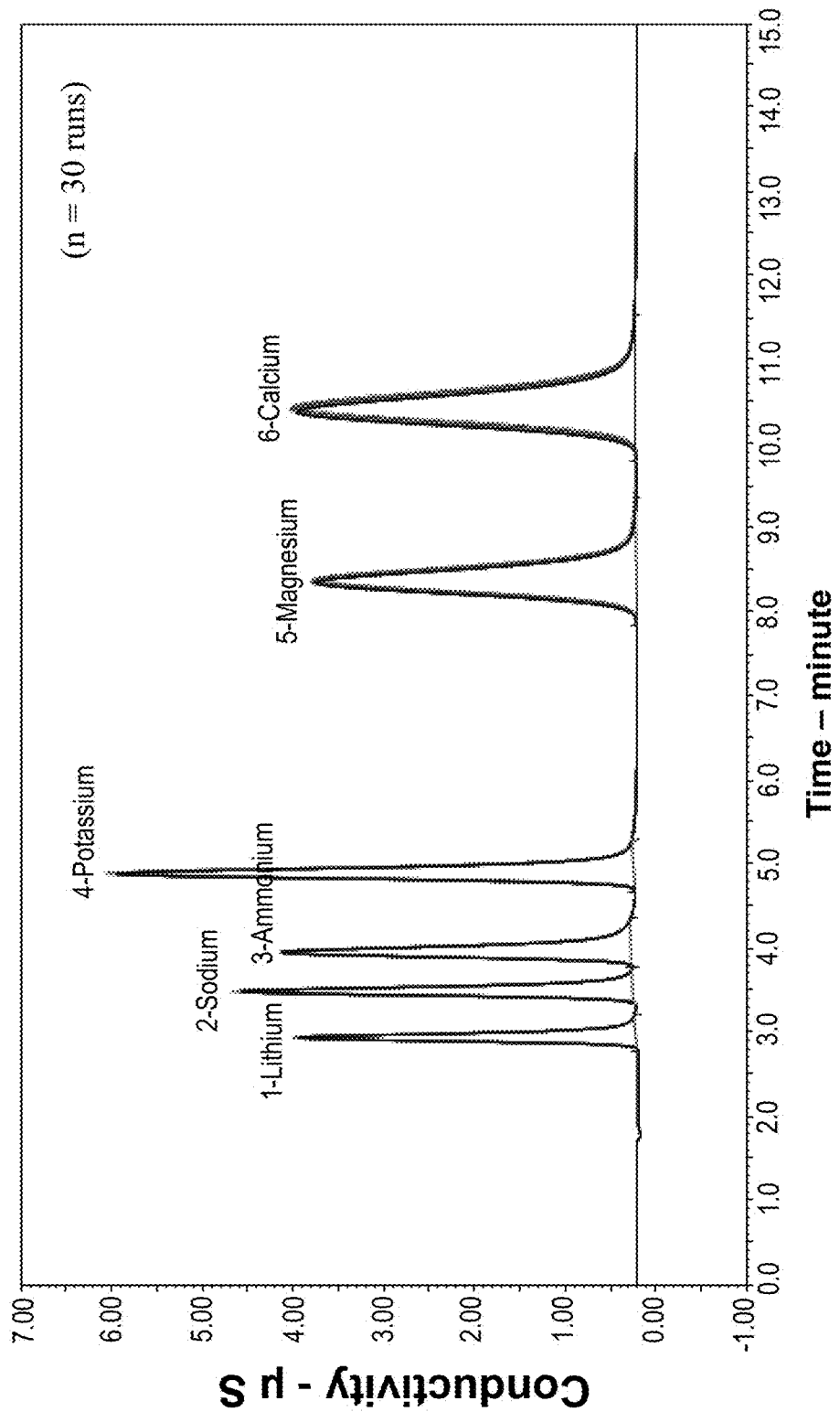
FIG. 21 shows thirty superimposed chromatograms illustrating excellent reproducibility of the cation separations using an apparatus in accordance with FIG. 1.

A CSRS device of the present invention was tested as per the configuration shown in FIG. 1 except only suppression was pursued. The unit was tested with a cation test matrix for 30 injections. The peak area RSD's showed an excellent reproducibility of the setup as shown in FIG. 21 and Table 4. These results indicate that the present device works well as a suppressor and shows reproducible performance for this key function. In addition the device is capable of pursuing sample prep applications as shown in the previous examples. The device of the present invention can also be used for the suppressor function if needed and this is illustrated in this example.

TABLE 4

| PeakArea Reproducibility Performance (% RSD) | |
|---|---|
| Peak Name | % RSD |
| 1 - Lithium | 0.168 |
| 2 - Sodium | 0.128 |

TABLE 4-continued

| PeakArea Reproducibility Performance (% RSD) | |
|---|---|
| Peak Name | % RSD |
| 3 - Ammonium | 0.1 |
| 4 - Potassium | 0.093 |
| 5 - Magnesium | 0.08 |
| 6 - Calcium | 0.072 |

Example 6

The device of FIG. 1 was used for sample pretreatment and suppression as per the present invention in the system of FIGS. 2-4. In this case, the sample comprised of a five anion standard that was dissolved in a sample containing 50 mM sodium hydroxide. The sample comprised a mixture of fluoride (Peak 1, 2.0 ppm), chloride (Peak 2, 3.0 ppm), Carbonate (Peak 3, Concentration not determined), Sulfate (Peak 4, 15 ppm), Nitrate (Peak 5, 10 ppm) and Phosphate (Peak 6, 15 ppm). A concentrator column was used in this application to concentrate a 20 µL injection of the sample anions prior to analysis. An AS15 (4×250 mm) column was used for the separation and was operated with 38 mM potassium hydroxide eluent at 1.2 mL/min. The suppressor of the present invention was operated with a current of 113 mA which is the recommended current for the standard three channel prior art suppressor. A control run was also pursued with a standard suppressor without sample pretreatment using a commercial ASRS 300 suppressor of the prior art. Under the conditions of the experiment without the sample pretreatment step, the commercial suppressor device showed poor recovery of the anions of interest as expected especially for the early elutors such as fluoride. In contrast the device of the present invention could pretreat the sample and remove the interfering matrix ions and therefore achieve good recovery of the analytes of interest was achieved as illustrated in FIGS. 22 and 23, and Table 5 that show the peak response in peak area counts. The peak area counts for fluoride for a sample without pretreatment was 0.0467 versus 0.5553 for the same peak but with sample pretreatment as per the present invention. This demonstrated that the device of the present invention was suited for sample pretreatment applications in conjunction with normal suppression function. Excellent peak shapes were observed with the device of the present invention.

TABLE 5

| Peak # | With out Sample Pretreatment | With Sample Pretreatment |
|---|---|---|
| 1 - Fluoride | 0.0467 | 0.5553 |
| 2 - Chloride | 0.1646 | 0.6218 |
| 3 - Carbonate | 0.684 | 2.0912 |
| 4 - Sulfate | 1.0254 | 2.4645 |
| 5 - Nitrate | 0.4336 | 1.1307 |
| 6 - Phosphate | 0.5456 | 0.9896 |

Example 7

The setup of the device of Example 2 was used in this experiment except the column was bypassed with a restrictor tubing that generated a pressure of about 1000 psi and the maximum suppression capacity of the device was studied by pumping in an eluent comprising of 200 mM sodium hydroxide. The double pass experiment was repeated with an applied current of 500 mA. The maximum suppression capacity was studied by monitoring the conductivity signal post suppression and by incrementally changing the flow rate from 1.0 mL/min by increments of 0.05 mL/min. If complete suppression was observed the background was low. Under these conditions the device of the present invention was able to suppress up to about 290 µeqv/min with an applied current of 500 mA. The above experiment was also repeated with a standard ASRS 300 suppressor which showed a suppression capacity of about 210 µeqv/min, which is significantly lower than the double pass approach. The above demonstrates the utility of the device of the present invention to suppress a higher concentration of eluent.

What is claimed is:

1. An electrolytic device suitable for use in pretreating a liquid sample and suppression, said electrolytic device comprising a housing including at least first, second, third, and fourth side-by-side liquid flow-through channels, each having an inlet and an outlet; said first channel being separated from said second channel by a first charged barrier having exchangeable ions capable of passing ions of only one charge, positive or negative, and of blocking bulk liquid flow; said second channel being separated from said third channel by a second charged barrier having exchangeable ions capable of passing ions of the same charge, positive or negative, and of blocking bulk liquid flow; said third channel being separated from said fourth channel by a third charged barrier having exchangeable ions capable of passing ions of the same charge, positive or negative, and of blocking bulk liquid flow; a first electrode disposed adjacent to and along said first channel in electrical communication therewith; and a second electrode disposed adjacent to and along said fourth channel in electrical communication therewith, wherein said first charged barrier, second charged barrier, and third charged barrier all have a same charge.

* * * * *